(12) United States Patent
Boileau et al.

(10) Patent No.: US 7,769,436 B1
(45) Date of Patent: Aug. 3, 2010

(54) SYSTEM AND METHOD FOR ADAPTIVELY ADJUSTING CARDIAC ISCHEMIA DETECTION THRESHOLDS AND OTHER DETECTION THRESHOLDS USED BY AN IMPLANTABLE MEDICAL DEVICE

(75) Inventors: Peter Boileau, Valencia, CA (US); Jay Snell, Studio City, CA (US); Rupinder Bharmi, Stevenson Ranch, CA (US); Laleh Jalali, Moorpark, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 567 days.

(21) Appl. No.: 11/757,796

(22) Filed: Jun. 4, 2007

(51) Int. Cl.
- *A61B 5/04* (2006.01)
- *A61B 5/0402* (2006.01)
- *A61B 5/0452* (2006.01)

(52) U.S. Cl. .................. 600/509; 600/517

(58) Field of Classification Search .............. 607/17; 600/509, 517
See application file for complete search history.

(56) References Cited

U.S. PATENT DOCUMENTS

| | | |
|---|---|---|
| 4,731,051 A | 3/1988 | Fischell |
| 4,947,845 A | 8/1990 | Davis |
| 5,113,869 A | 5/1992 | Nappholz et al. |
| 5,135,004 A | 8/1992 | Adams et al. |
| 5,199,428 A | 4/1993 | Obel et al. |
| 5,203,326 A | 4/1993 | Collins |
| 5,313,953 A | 5/1994 | Yomtov et al. |
| 5,328,460 A | 7/1994 | Lord et al. |
| 5,615,684 A | 4/1997 | Hagel et al. |
| 5,676,141 A | 10/1997 | Hollub |
| 5,960,797 A | 10/1999 | Kramer et al. |
| 6,016,443 A | 1/2000 | Ekwall et al. |
| 6,021,350 A | 2/2000 | Mathson |
| 6,108,577 A | 8/2000 | Benser |
| 6,112,116 A | 8/2000 | Fischell et al. |
| 6,115,628 A | 9/2000 | Stadler et al. |
| 6,128,526 A | 10/2000 | Stadler et al. |
| 6,233,486 B1 | 5/2001 | Ekwall et al. |
| 6,249,705 B1 | 6/2001 | Snell |
| 6,256,538 B1 | 7/2001 | Ekwall |
| 6,264,606 B1 | 7/2001 | Ekwall et al. |
| 6,272,379 B1 | 8/2001 | Fischell et al. |

(Continued)

FOREIGN PATENT DOCUMENTS

EP        1102196        5/2001

(Continued)

*Primary Examiner*—Carl H Layno
*Assistant Examiner*—Yun Haeng Lee

(57) ABSTRACT

Techniques are described for adaptively adjusting detection thresholds for use in detecting cardiac ischemia and other abnormal physiological conditions based on morphological parameters derived from intracardiac electrogram (IEGM) signals, impedance measurements, or other signals. In one example, where ST segment elevation is used to detect cardiac ischemia, default detection thresholds are determined in advance from an examination of variations in ST segment elevations occurring within a population of patients. Thereafter, an individual pacemaker or other implantable medical device uses the default thresholds during an initial learning period to detect ischemia within the patient in which the device is implanted. During the initial learning period, the pacemaker also collects data representative of the range of variation in ST segment elevations occurring within the patient. The pacemaker then adaptively adjusts the thresholds based on the range of variation so as to improve detection specificity within the patient.

11 Claims, 17 Drawing Sheets

U.S. PATENT DOCUMENTS

| | | |
|---|---|---|
| 6,377,852 B1 | 4/2002 | Bornzin et al. |
| 6,381,493 B1 | 4/2002 | Stadler et al. |
| 6,468,263 B1 | 10/2002 | Fischell et al. |
| 6,501,983 B1 | 12/2002 | Natarajan et al. |
| 6,519,493 B1 | 2/2003 | Florio et al. |
| 6,539,259 B1 * | 3/2003 | Weinberg et al. ............. 607/9 |
| 6,575,912 B1 | 6/2003 | Turcott |
| 6,609,023 B1 | 8/2003 | Fischell et al. |
| 6,788,970 B1 | 9/2004 | Park et al. |
| 6,985,771 B2 | 1/2006 | Fischell et al. |
| 7,107,096 B2 | 9/2006 | Fischell et al. |
| 7,142,911 B2 | 11/2006 | Boileau et al. |
| 2004/0077962 A1 | 4/2004 | Kroll |
| 2005/0240233 A1 | 10/2005 | Lippert et al. |
| 2006/0009810 A1 | 1/2006 | Mann et al. |
| 2006/0149155 A1 | 7/2006 | Hedberg |
| 2006/0149331 A1 | 7/2006 | Mann et al. |

FOREIGN PATENT DOCUMENTS

| | | |
|---|---|---|
| EP | 1011432 | 12/2004 |
| WO | WO2004/058334 | 7/2004 |

\* cited by examiner

SYSTEM AND METHOD FOR ADAPTIVELY ADJUSTING CARDIAC ISCHEMIA DETECTION THRESHOLDS AND OTHER DETECTION THRESHOLDS USED BY AN IMPLANTABLE MEDICAL DEVICE

FIELD OF THE INVENTION

The invention generally relates to implantable medical devices such as pacemakers and implantable cardioverter/defibrillators (ICDs) and, in particular, to techniques for detecting cardiac ischemia, hypoglycemia, hyperglycemia and other abnormal physiological conditions using such devices.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting cardiac ischemia in real-time so that the victim may be warned and medical attention sought. If properly warned, surgical procedures may be implemented to locate and remove the growing arterial blockage or anti-thrombolytic medications may be administered. At the very least, such warnings would allow the victim to cease activities that might result in a fatal accident. Moreover, in many cases, AMI or VF is triggered by strenuous physical activities and so ischemia warnings would allow the victim to cease such activities, possibly preventing AMI or VF from occurring.

Many patients at risk of cardiac ischemia have pacemakers, ICDs or other medical devices implanted therein, or are candidates for such devices. Accordingly, techniques have been developed for detecting cardiac ischemia using implanted medical devices. In particular, techniques have been developed for analyzing intracardiac electrogram (IEGM) signals sensed by such devices in an effort to detect cardiac ischemia. See, for example, U.S. Pat. No. 6,108,577 to Benser, entitled "Method and Apparatus for Detecting Changes in Electrocardiogram Signals." See, also, U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al.; 6,016,443, 6,233,486, 6,256,538, and 6,264,606 to Ekwall; 6,021,350 to Mathson; 6,112,116 and 6,272,379 to Fischel) et al; 6,128,526, 6,115,628 and 6,381,493 to Stadler et al; and. Many IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). Herein, the ST segment elevation pertains to the amplitude of the ST segment relative to some isoelectric baseline and hence can be positive or negative. A change in the ST segment elevation is referred to herein as an ST segment deviation, i.e. ST segment deviation refers to a change in ST segment elevation relative to a historical elevation baseline. The QRS complex usually follows an atrial depolarization (also referred to as a P-wave.) Strictly speaking, P-waves, R-waves and T-waves are features of a surface electrocardiogram (EKG). For convenience and generality, the terms P-wave, T-wave and T-wave are used herein to refer to the corresponding internal signal component as well.

Typically, the amount of deviation, if any, from a baseline ST segment elevation is compared by the implanted device against a predetermined threshold. If the amount of deviation exceeds the threshold, cardiac ischemia is deemed to have occurred. Warning signals may be generated and, in at least some devices, therapy may be automatically adjusted in response to the ischemia. Often, the threshold is set by the physician during a programming session following device implant but is not otherwise adjusted. Although ST segment elevation is often exploited, other parameters derived from morphological features of the IEGM can instead be used. Other parameters that potentially may be exploited to detect cardiac ischemia include various duration-based parameters such as P-wave width, QRS-complex width and T-wave width; various slope-based parameters such as maximum P-wave slope, maximum QRS-complex slope and maximum T-wave slope; various amplitude-based parameters such as peak P-wave amplitude, peak QRS-complex amplitude and peak T-wave amplitude; as well as various interval-based parameters such as atrioventricular (AV) intervals and the aforementioned ST intervals. Also, devices may exploit the interval between the beginning of a QRS complex and the maximum amplitude (i.e. the peak) of a corresponding T-wave as well as the interval between the beginning of the QRS complex and the end of the corresponding T-wave. These intervals are referred to herein, respectively, as the QTmax interval and the QTend interval. For further discussions regarding various intervals that may be appropriate, alone or in combination with one another, for detecting cardiac ischemia, see U.S. patent application Ser. No. 11/394,724, of Ke et al., filed Mar. 31, 2006, entitled "Ischemia Detection using T-wave Amplitude, QTmax and ST Segment Elevation and Pattern Classification Techniques," which is incorporated by reference herein. See, also, U.S. Pat. Nos. 7,107,096, 6,985,771, 6,609,023, 6,468,263, 6,272,379, and 6,112,116, each to Fischell et al.

Determining how to set detection thresholds presents a challenge. Any feature measurement used to detect cardiac ischemia is likely to vary somewhat with time even in the absence of ischemia. Variability may occur due to changes in posture, autonomic tone, heart rate, activity level, etc. This is known to be the case with ST segment elevation. The amount of variation in the ST segment, and in other parameters, also may vary significantly from patient to patient. As noted, the detection threshold is often set for a particular patient by the physician during a programming session following device implant. If the threshold is set fairly close to a baseline ST segment elevation for the patient (i.e. the threshold is set conservatively) and there is considerable variation in ST segment elevation within that patient in the absence of ischemia, frequent false alarms will likely occur. On the other hand, if the threshold is set fairly far from the baseline ST segment elevation for the patient (i.e. the threshold is set more liberally) and there is relatively little variation in ST segment elevation within that patient even during ischemia, then actual episodes of ischemia may not be properly detected. Similar problems can potentially arise with any of the other ischemia detection parameters.

Accordingly, it would be desirable to provide improved techniques for setting ischemia detection threshold and it is to this end that various aspects of the present invention are directed.

Although the detection of cardiac ischemia is of paramount importance since ischemia may be a precursor to a potentially fatal AMI or VF, it is also desirable to detect hypoglycemia, hyperglycemia, or other abnormal physiological conditions so as to provide suitable warning signals. Diabetic patients, particular, need to frequently monitor blood glucose levels to ensure that the levels remain within acceptable bounds and, for insulin dependent diabetics, to determine the amount of insulin that must be administered. Various threshold-based detection techniques have been developed for detecting hypoglycemia and hyperglycemia based on features of electrical cardiac signals, particularly ST segments and T-waves. See, for example, U.S. patent application Ser. No. 11/043,612, of Gill et al., filed Jan. 25, 2005, entitled "System and Method for Distinguishing Among Ischemia, Hypoglycemia and Hyperglycemia Using an Implantable Medical Device", which is incorporated by reference herein. See, also, U.S. patent application Ser. No. 11/127,370, of Bharmi, filed May 11, 2005, entitled "System and Method for Distinguishing Between Hypoglycemia and Hyperglycemia Using an Implantable Medical Device" (which is a CIP of application Ser. No. 11/043,612) and U.S. patent application Ser. No. 11/117,624, also of Bharmi, filed Apr. 27, 2005, entitled "System and Method for Detecting Hypoglycemia Based on a Paced Depolarization Integral Using an Implantable Medical Device".

Accordingly, it would be also desirable to provide improved techniques for setting the detection thresholds associated within other abnormal physiological conditions besides ischemia and it is to this end that various aspects of the present invention are directed.

SUMMARY OF THE INVENTION

In accordance with an exemplary embodiment, a method is provided for use with an implantable medical device such as a pacemaker or ICD wherein the device has a detection system that detects an abnormal physiological condition, e.g. cardiac ischemia, hyperglycemia or hypoglycemia, within the patient in which the device is implanted. The detection system compares at least one morphological parameter— derived from signals sensed within the patient—against a detection threshold. In one example of the method, electrical cardiac signals such as IEGM signals are then sensed within the patient and values of the morphological parameter are derived from the electrical cardiac signals. In another example, impedance signals are detected. In still other examples, physiological signals such as pressure values are detected. In any case, the values of the morphological parameter are monitored by the system to detect a possible occurrence of the abnormal physiological condition. Additionally, information representative of a range of variation in the morphological parameter within the patient is collected by the implanted device. In one particular example, the detection threshold is initially set to a default value, which may be a fairly conservative threshold value. The abnormal physiological condition is detected by comparing the values of the morphological parameter against the default threshold.

The detection threshold is then automatically adjusted by the implanted device based on the information representative of the range of variation in the morphological parameter collected within the patient so as to improve detection accuracy. For example, if the default threshold is too conservative based on the range of variation of the morphological parameter within a particular patient (resulting in frequent false alarms within that patient), the threshold is automatically adjusted by the implanted device to reduce the number of false alarms. Conversely, if the default threshold is too liberal in view of the range of variation of the morphological parameter within the patient (such that actual episodes of the abnormal physiological state might not be initially detected with the patient), the threshold is automatically adjusted to ensure such conditions are properly detected.

In an illustrative implementation, the implanted device is equipped to detect episodes of cardiac ischemia based on deviations in ST segment elevation from a baseline within the patient. The default value is set based on a range of variation in ST segment elevations observed within a population of human test subjects as determined using an external system. The default threshold may be set, for example, to a relatively conservative value as determined based, e.g., on a predetermined percentile value applied to the observed data. Advantageously, histograms may be employed to collected data from the population of test subjects for ease in determining an appropriate default threshold. The default value is then programmed into a pacemakers and ICDs for implant within various patients. In one specific example, the default threshold is set to detect ischemia based on a 20% deviation from a baseline ST segment elevation. That is, any increase or decrease of the ST segment elevation of more then 20% (from the baseline ST segment elevation of the patient) is deemed to be indicative of cardiac ischemia. Depending upon the implementation, ST segments derived from X out of Y heartbeats must meet this criterion for ischemia to be indicated (where, e.g., X is 7 and Y is 10), or X heartbeats must meet the criteria within a predetermined interval of time.

Each individual implanted device uses this same default threshold value during an initial learning period following implant of the device into a respective patient. Data regarding actual ST segment elevation variability within the patient is collected by the implanted device, again preferably using histograms. Upon completion of the learning period within a given patient, the device implanted within that patient then adjusts the threshold it uses based on the range of variation of ST segment elevations observed within that particular patient during the learning period so as to improve detection specificity. For example, if the patient was found to exhibit a wide range of variability in ST segment elevations, the threshold may be adjusted by the device to require a greater percentage deviation (perhaps 25%) in ST segment elevation to detect ischemia so as to reduce false alarms. If, on the other hand, the patient was found to exhibit a narrow range of variability in ST segment elevations, the threshold may instead be adjusted by the device to require a much lower percentage deviation (perhaps only 5%) in ST segment elevations to detect ischemia so as to help ensure that actual episode of ischemia are properly detected. The adjustment of the thresholds may be based on percentile values, as well. Separate upper and lower threshold may be used, which need not be symmetric. For example, for a particular patient, an increase in ST segment elevation of 10% above the baseline elevation may be deemed to be indicative of ischemia; whereas only a 5% decrease in ST segment elevation below the baseline elevation may be deemed to be indicative of ischemia. The thresholds may be self-normalizing.

A wide variety of other parameters besides ST segment elevation may be used, depending upon the particular abnormal physiological condition to be detected. Other parameters that potentially may be exploited include duration-based parameters such as P-wave width, QRS-complex width and T-wave width; slope-based parameters such as maximum P-wave slope, maximum QRS-complex slope and maximum T-wave slope; amplitude-based parameters such as peak P-wave amplitude, peak QRS-complex amplitude and peak T-wave amplitude; as well as various interval-based parameters such as atrioventricular (AV) intervals, and the aforementioned QTmax and QTend intervals. In many cases, multiple parameters will be used to further improve detection specificity, with each parameter having one or more separate detection thresholds associated therewith, each individually adjustable by the device.

Separate thresholds may also be defined for use under different patient conditions such as time of day, heart rate, posture, and activity level. For example, separate time of day-based detection thresholds may be used including one or more of: a morning detection threshold, an afternoon detection threshold and an evening/night detection threshold. That is, for each individual physiological parameter to be monitored, such as ST segment elevation, the implanted devices may use one threshold in the morning, a different threshold in the afternoon, and still yet another threshold in the evenings and at night. The different ST segment elevation thresholds are each separately adjustable based on data collected within the patient during those times of the day. Likewise, thresholds for use with any of the other morphological parameters (such as QTmax or QTend thresholds) may be specified for use at different times of day, if warranted. As another example, separate heart rate-based detection thresholds may be used including one or more of: a low heart rate threshold, a medium heart rate threshold and a high heart rate threshold. As yet another example, separate posture-based detection thresholds may be used including one or more of: an upright posture threshold, a supine posture threshold, a prone posture threshold, a left-side lying posture threshold and a right-side lying posture threshold. As still yet another example, separate activity-based detection thresholds may be used including one or more of: a low activity level threshold, a medium activity level threshold and a high activity level threshold. Advantageously, a multidimensional histogram having separate cells for each combination of time of day, heart rate, posture, activity level, as well as for each morphological parameter and each percentile range of values of that parameter, may be employed by the device, depending upon device memory.

Also, multiple thresholds may be exploited for use with the same morphological parameter, which take into account persistence. For example, upper and lower ST segment deviation thresholds may be defined. If the ST segment deviation exceeds the upper ST-based threshold, ischemia is thereby detected, even if the ST segment remains elevated for only a relatively short period of time, such as one minute. However, if the ST segment deviation only exceeds the lower ST-based threshold, ischemia is thereby detected only if the deviation persists over some longer period of time, such as fifteen minutes. That is, in this example, a relatively mild ischemia is detected only if it is persistent. A more severe episode of ischemia is detected based solely on the amount of ST segment deviation. In other examples, mild ischemia is detected whenever the ST segment deviation exceeds the lower threshold. The mild ischemia is reclassified as severe if it persists for more than fifteen minutes. The various threshold adjustment techniques summarized above also apply to these persistence-based detection procedures.

Upon detecting of the onset of an episode of cardiac ischemia or other abnormal physiological condition, appropriate warning signals are generated, which can include both "tickle warning" signals applied to subcutaneous tissue and short range telemetry warning signals transmitted to a device external to the patient. Therapy may also be applied or modified by the implanted system in response to the detected condition, depending upon the capabilities of the implanted system. For example, if the implanted system is equipped with a drug pump, appropriate medications may be administered such as anti-thrombolytic drugs for ischemia or insulin for hyperglycemia. If overdrive pacing is being applied by the system, overdrive pacing is preferably deactivated to prevent the increased heart rate associated with overdrive pacing from exacerbating the ischemia. If the system has defibrillation capabilities, the system may immediately begin charging defibrillation capacitors upon detection of cardiac ischemia to permit prompt delivery of a defibrillation shock if the ischemia triggers VF. Additionally, or in the alternative, diagnostic information pertaining to the detected condition may be stored for subsequent review by a physician. Lower thresholds may be used to trigger recording of diagnostics, with higher thresholds to triggering warnings, and still higher thresholds used to trigger automatic delivery of therapy.

In some cases, it may be appropriate to reinitialize or reset the various thresholds. For example, if the ST segment elevation remains shifted for days or weeks, such is probably not indicative of a true ischemia, but is probably due to changes in medications or other factors. Hence, the implantable device preferably repeats the adaptive adjustment procedures after resetting the thresholds to their default values. Appropriate diagnostic information indicating the reinitialization procedure is preferably stored. Warnings might also be generated to notify the physician of the need to reinitialize the procedure.

Hence, improved techniques are provided for detecting cardiac ischemia or other abnormal physiological conditions. The techniques are preferably performed by the implanted medical device itself to provide prompt warnings of abnormal conditions and to deliver appropriate therapy. Alternatively, the techniques may be performed by external devices, such as bedside monitors or the like, based on IEGM signals detected by the implanted device and transmitted to the external device. System and method implementations of the techniques are described herein.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
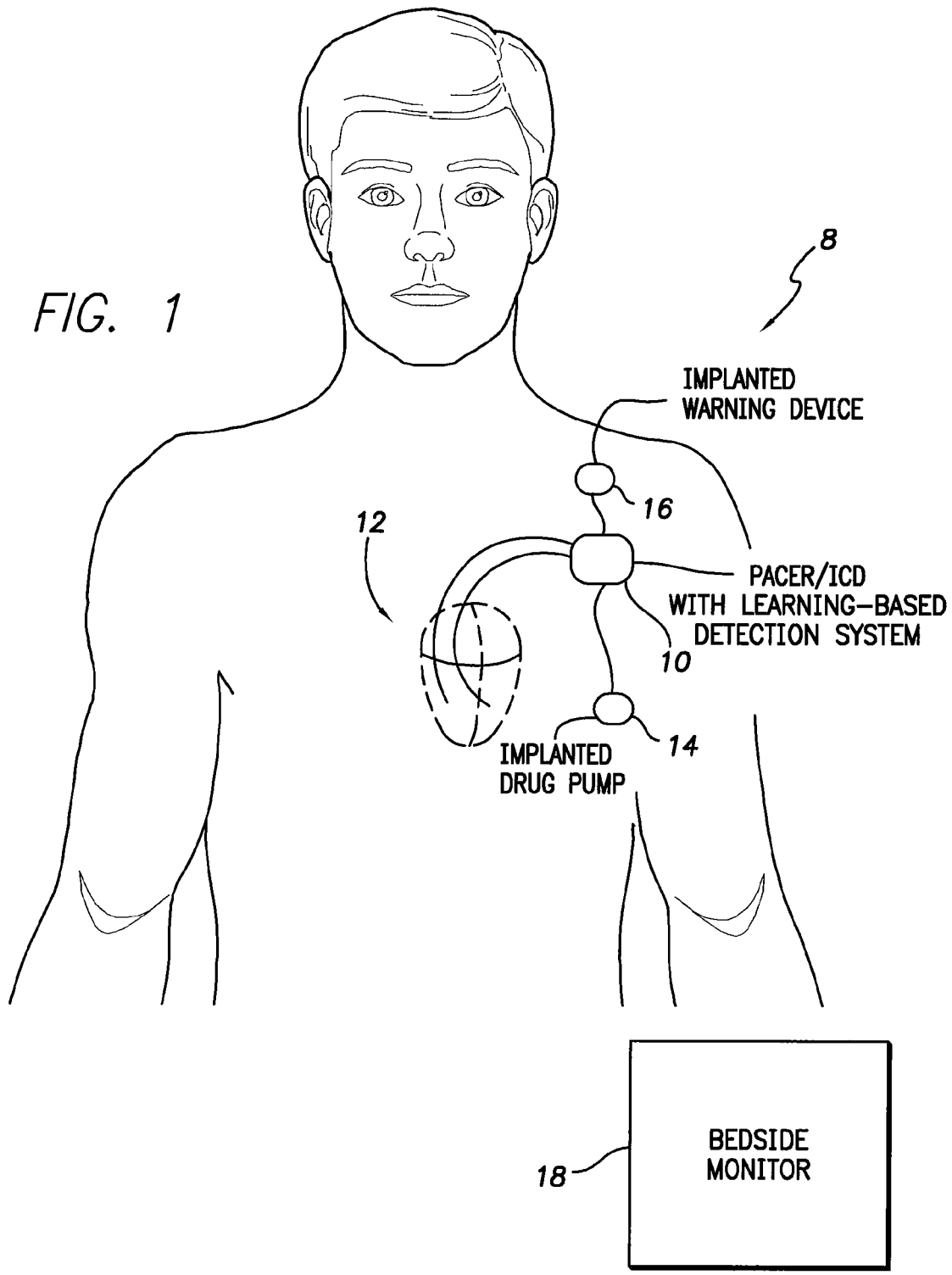
FIG. 1 illustrates pertinent components of an implantable medical system having a pacemaker or ICD capable of adaptively adjusting detection thresholds for use in detecting cardiac ischemia or other abnormal physiological conditions and for delivering therapy or warning signals in response thereto.

FIG. 1 illustrates an implantable medical system 8 capable of detecting cardiac ischemia or other abnormal physiological conditions such as hypoglycemia or hyperglycemia. To this end, system 8 includes a pacer/ICD 10 or other cardiac stimulation device equipped with a learning-based detection system equipped to adaptively adjust detection thresholds for use in detecting cardiac ischemia for optimal use within the particular patient in which the system is implanted. The learning-based detection system may additionally, or alternatively, be equipped to adaptively adjust detection thresholds associated with hypoglycemia, hyperglycemia, or other abnormal physiological conditions. The pacer/ICD also includes internal components for controlling the delivery of therapy and warnings in response to the detection of any such abnormal physiological conditions.

Figure 16:
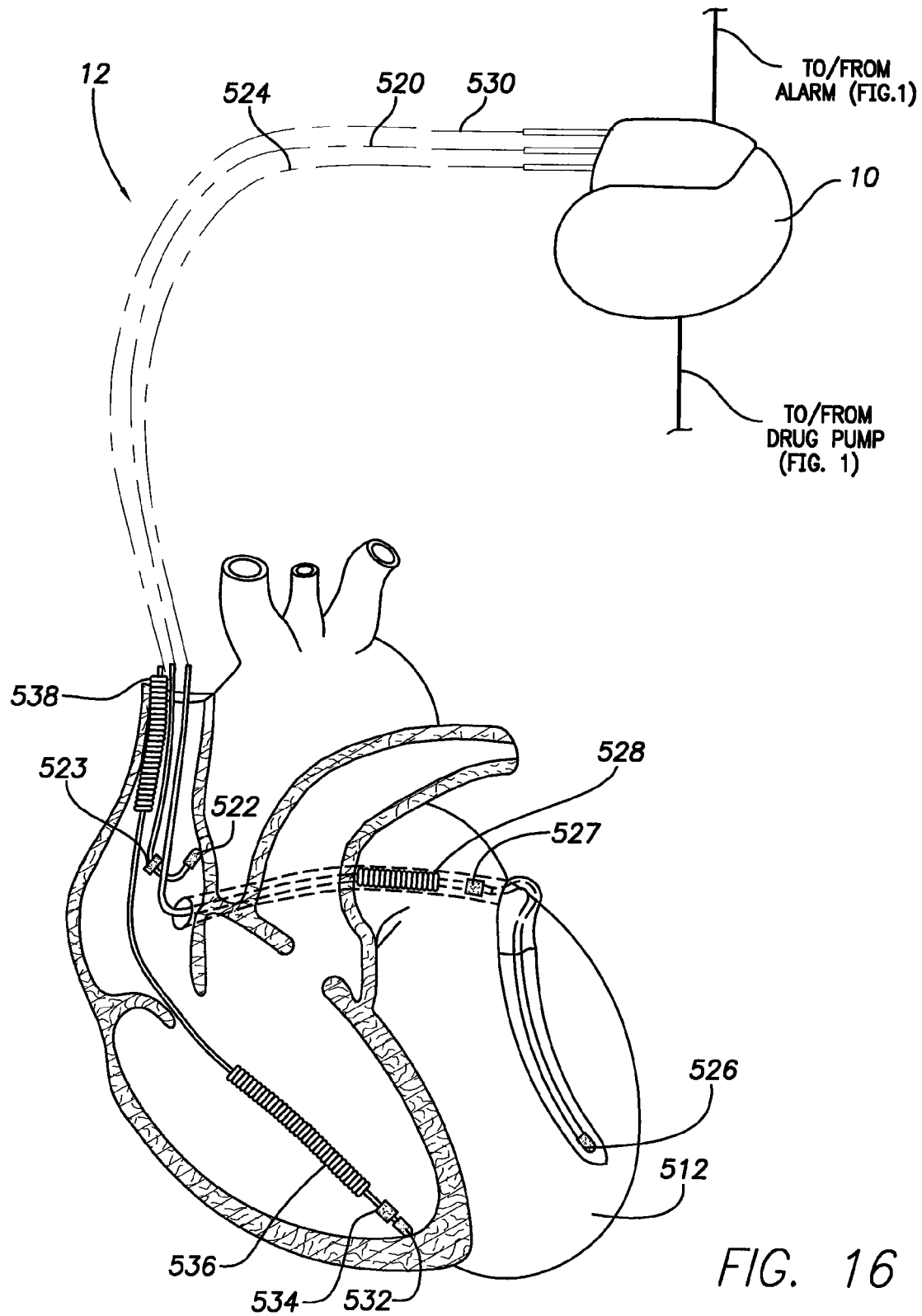
FIG. 16 is a simplified, partly cutaway view, illustrating the pacer/ICD of FIG. 1 along with at full set of leads implanted into the heart of the patient.

To detect an abnormal physiological condition, pacer/ICD 10 senses IEGM signals or electrical cardiac signals, identifies selected morphological parameters therein and then compares values representative of those parameters against thresholds appropriate for that abnormal physiological condition. More specifically, the pacer/ICD receives electrical cardiac signals from a set of cardiac pacing/sensing leads 12 implanted on or within the heart of the patient from which the IEGM is derived. In FIG. 1, only two pacing leads are shown. A more complete set of pacing leads is shown in FIG. 16, discussed below. The pacer/ICD then derives or extracts selected morphological parameters from the IEGM signals based upon the abnormal condition to be detected. For cardiac ischemia, for example, ST segment elevations may be derived, alone or in combination with other morphological parameters affected by ischemia such as QTmax and QTend values. The morphological parameters are then compared against one or more thresholds indicative of ischemia. Initially, the thresholds are set to default values determined by an external system from an analysis of ST segment elevation variability data obtained from a population of test subjects, typically other patients. The thresholds are adaptively adjusted, by the pacer/ICD, based on a range of variability in the morphological parameters exhibited within the particular patient in whom the pacer/ICD is implanted, so as to improve detection specificity or sensitivity within that patient. Different thresholds may be employed under different conditions, such as different heart rates, postures, etc. This will all be explained in greater detail below. The same adaptive procedures may applied to the thresholds employed to detect other abnormal physiological conditions, such as hyperglycemia and hypoglycemia, If an abnormal physiological condition is detected, appropriate therapy may be automatically delivered by the implantable system under the control of the pacer/ICD. For example, for ischemia, anti-thrombolytics or other appropriate medications may be automatically delivered directly to the patient via an implanted drug pump 14, if one is provided. Implantable devices for delivering anti-thrombolytic drugs are discussed in U.S. Pat. No. 5,960,797 to Kramer, et al. The pacer/ICD may also change pacing parameters in response to the detection of ischemia to, for example, deactivate overdrive pacing, which may exacerbate the ischemia. Other forms of elevated pacing may be discontinued as well, such as atrial fibrillation (AF) suppression therapy or activity-based rate responsive pacing. Various techniques for controlling delivery of therapy in response to ischemia are discussed in U.S. Pat. No. 6,256,538 to Ekwall, listed above. See also U.S. Pat. No. 6,377,852 to Bornzin et al., which provides techniques for slowing the heart rate in response to ischemia. In addition, if the device is an ICD, then it may be controlled to immediately begin charging defibrillation capacitors in expectation of delivery of a defibrillation shock, which may be needed if the ischemia triggers VF. This is particularly appropriate if the ischemia is severe. As another example, for hypoglycemia, the device may use the drug pump to deliver insulin, particularly if the patient is known to be diabetic. Techniques for controlling delivery of therapy in response to hypoglycemia are set forth in U.S. Patent Application Number 2004/0077962 of Kroll, published Apr. 22, 2004, entitled "System and Method for Monitoring Blood Glucose Levels Using an Implantable Medical Device". Information regarding implantable insulin pumps may be found in U.S. Pat. No. 4,731,051 to Fischell and in U.S. Pat. No. 4,947,845 to Davis.

Warning signals may additionally, or alternatively, be generated. For example, if ischemia is detected, the patient is warned by application of an internal perceptible "tickle" notification signal using an implanted warning device 16. "Tickle" warning device are discussed in U.S. Pat. No. 5,328,460 to Lord, et al., entitled "Implantable Medication Infusion Pump Including Self-Contained Acoustic Fault Detection Apparatus." If the device is configured to generate warning signals for other conditions, such as hyperglycemia or hypoglycemia, the device preferably employs different notification signal frequencies for the different warnings so that the patient can properly distinguish between different warnings. In addition, warning signals may be transmitted using a short-range telemetry system to a bedside monitor 18 or to a handheld warning device (not separately shown) using techniques described within U.S. patent application Ser. No. 10/603,429, entitled "System And Method For Detecting Cardiac Ischemia Using An Implantable Medical Device", of Wang et al., filed Jun. 24, 2003. The bedside monitor or handheld warning device provides audible or visual alarm signals to alert the patient, as well as textual or graphic displays. The bedside monitor or handheld warning device thereby provides confirmation of the warning to the patient, who may be otherwise uncertain as to the reason for the internally generated tickle warning signal.

In addition, once an abnormal physiological condition has been detected, diagnostic information is generated within the pacer/ICD for transmission to the bedside monitor or for subsequent transmission to an external programmer (not shown in FIG. 1) for review by a physician or other medical professional. The physician may then prescribe any other appropriate therapies to prevent additional episodes of the abnormal condition. The physician may also adjust the operation of the pacer/ICD to activate, deactivate or otherwise control any therapies that are automatically applied. The bedside monitor may be directly networked with a centralized computing system, such as the HouseCall™ system of St. Jude Medical, for immediately notifying the physician of the abnormal condition, particular if it appears dangerous, such as if the ischemia is an acute myocardial ischemia. Networking techniques for use with implantable medical systems are set forth, for example, in U.S. Pat. No. 6,249,705 to Snell, entitled "Distributed Network System for Use with Implantable Medical Devices." Note that a lower threshold may be used to trigger recording of diagnostics, with a higher threshold used for triggering warnings, and a still higher threshold for triggering automatic delivery of therapy. Moreover, the thresholds may be self-normalizing as described in the above-cited references, particularly those of Fischell et al.

Hence, FIG. 1 provides an overview of an implantable system having a learning-based detection system for detecting cardiac ischemia, hypoglycemia, hyperglycemia or other abnormal physiological conditions and for delivering appropriate therapy or warnings. Systems provided in accordance with the invention need not include all the components shown in FIG. 1. In many cases, for example, the system will include only the pacer/ICD and its leads. Drug pumps and warning devices are not necessarily implanted. In addition, although internal signal transmission lines are illustrated in FIG. 1 for interconnecting the various implanted components, wireless signal transmission may alternatively be employed. Furthermore, the particular locations and relative sizes of the implanted components shown in FIG. 1 are merely illustrative and may not necessarily correspond to actual implant locations or relative sizes.

Overview of the Learning-Based Detection Technique

Figure 2:
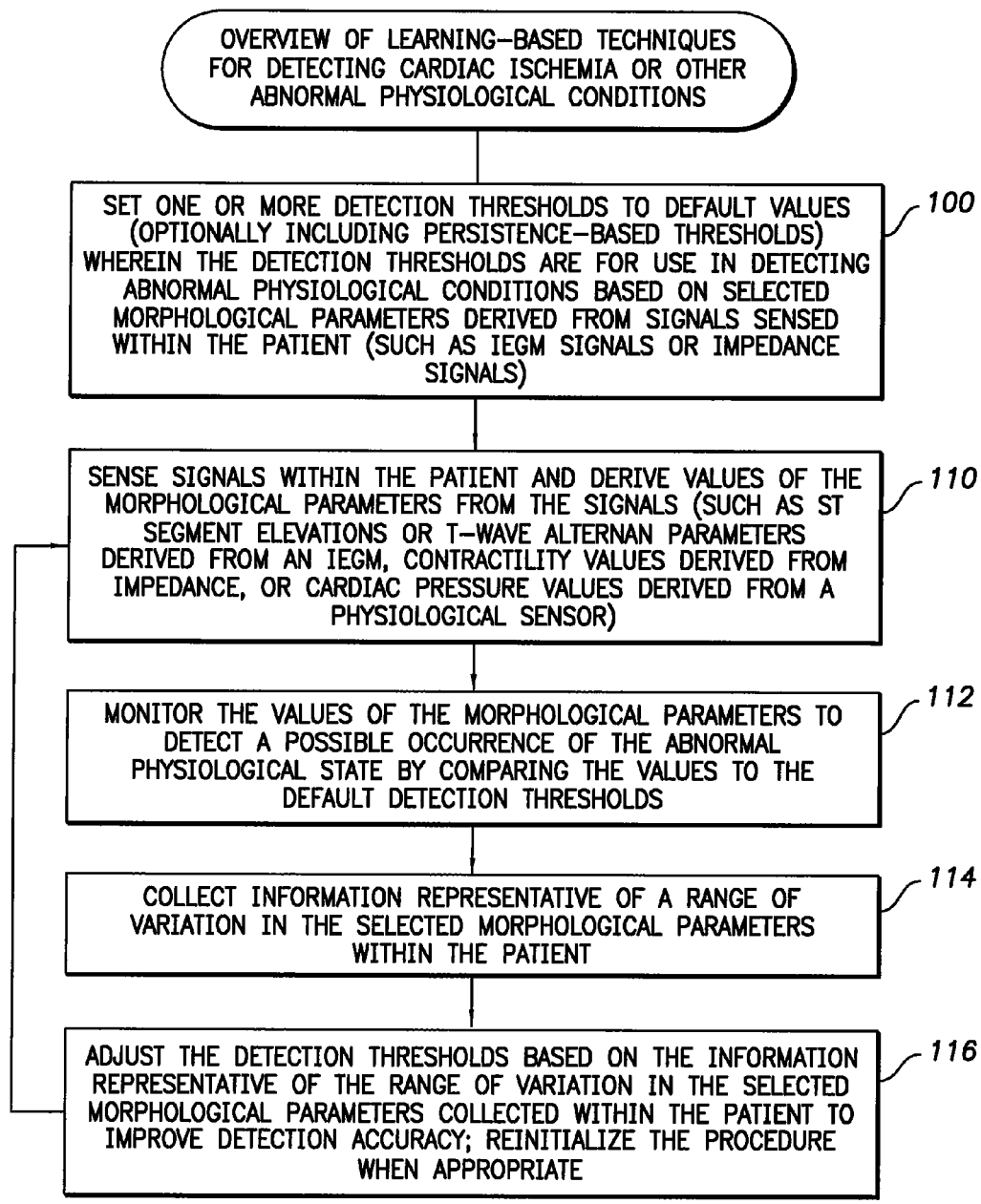
FIG. 2 is a flow diagram providing an overview of a technique for setting and adjusting detection thresholds that may be performed by the system of FIG. 1.
Figure 3:
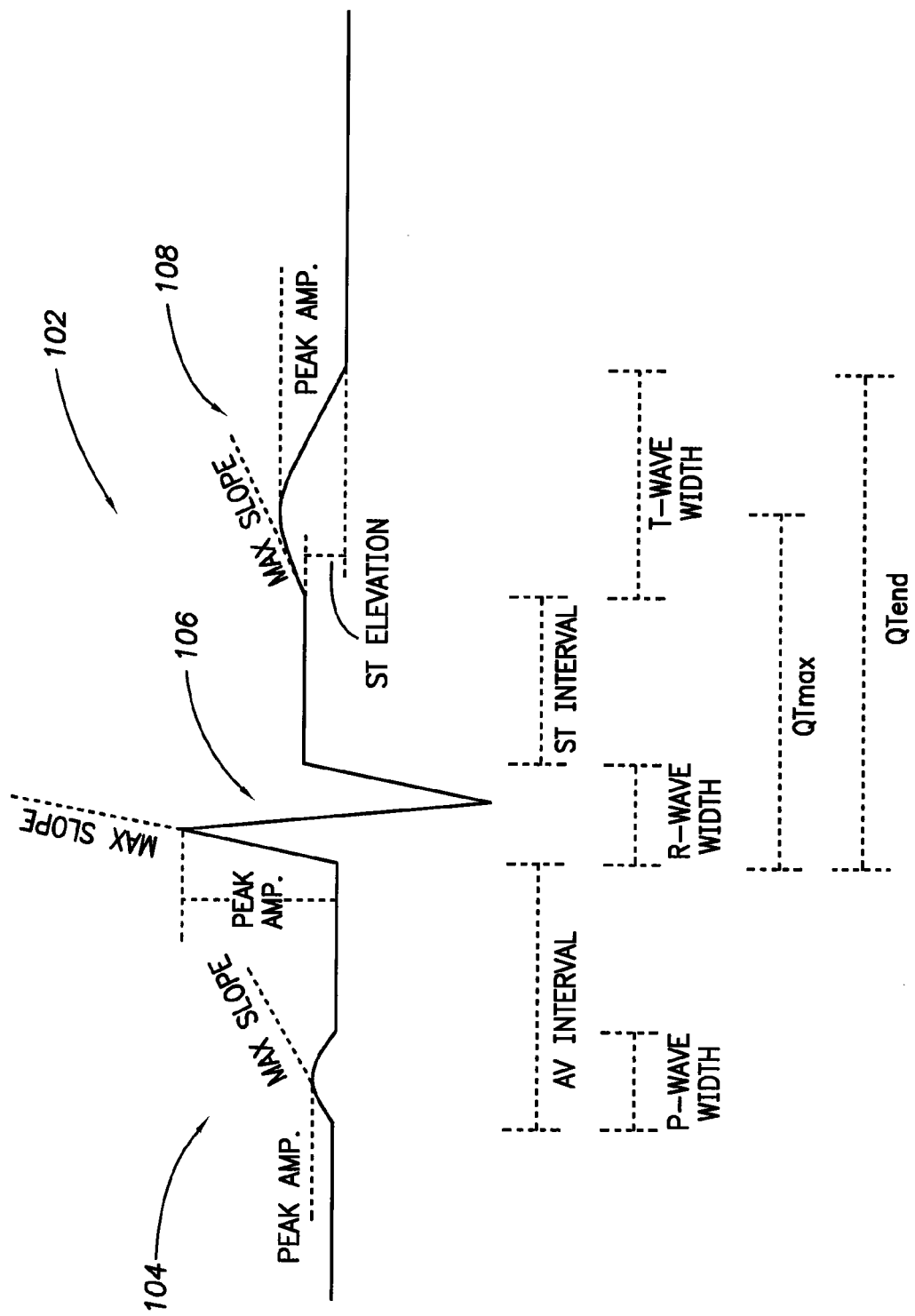
FIG. 3 sets forth a stylized diagram of an IEGM of an individual heartbeat, particularly illustrating various morphological parameters that may be derived from the IEGM for use in detecting abnormal physiological conditions subject to detection thresholds that may be adjusted using the technique of FIG. 2.
Figure 4:
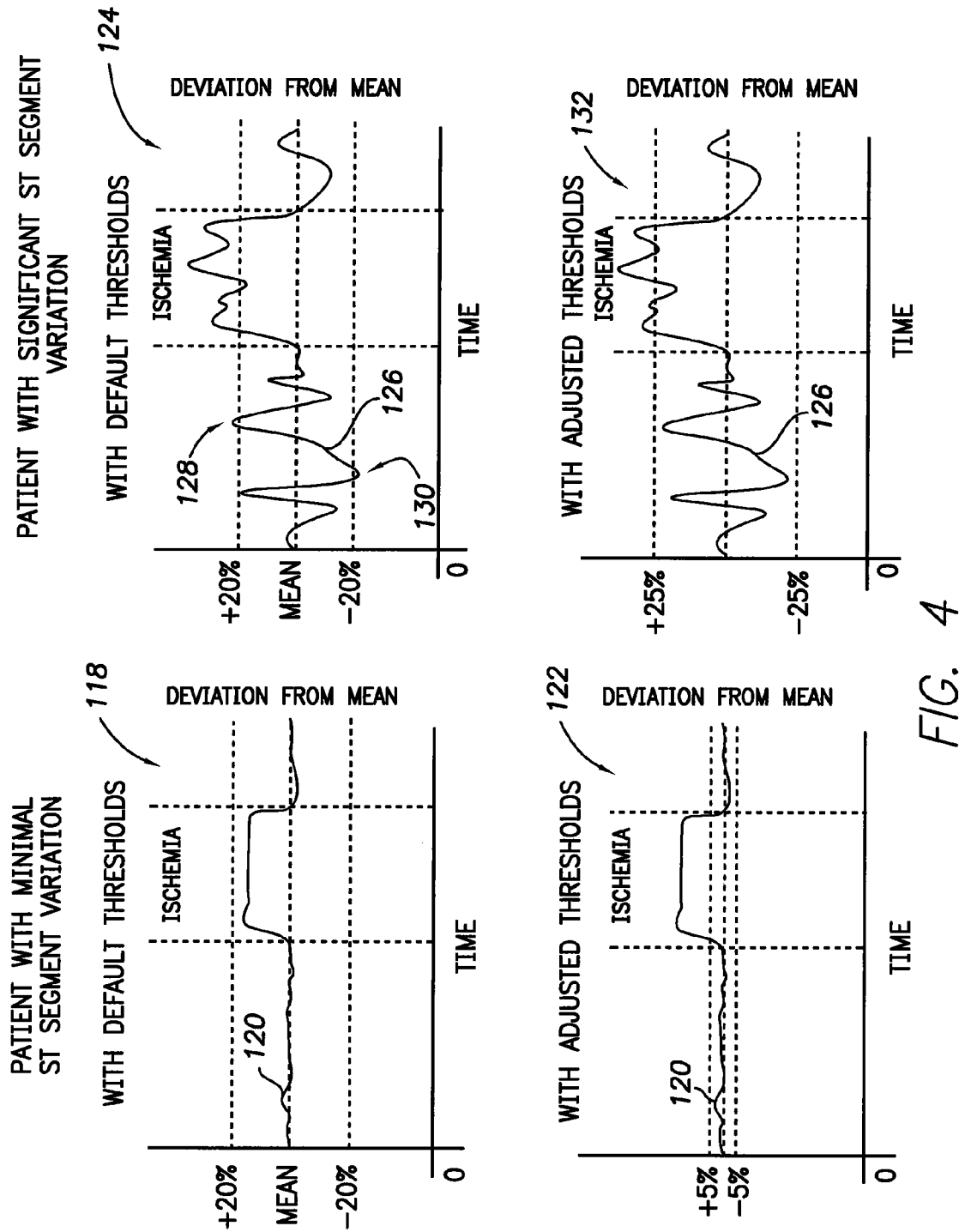
FIG. 4 sets forth stylized graphs of exemplary changes in ST segment elevation over time with two different patients and particularly illustrating adaptive modification of ischemia detection thresholds that may be performed using the adjustment technique of FIG. 2.

FIGS. 2-4 summarize the learning-based detection technique that may be performed using the system of FIG. 1 for adaptively adjusting detection thresholds. Briefly, at step 100 of FIG. 2, the pacer/ICD sets one or more detection thresholds to default values, wherein the detection thresholds are for use in detecting an abnormal physiological condition based on selected morphological parameters derived from signals sensed within the patient (such as IEGM signals, impedance signals or physiological sensor signals). The default values are preferably determined in advance based on data observed within populations of test subjects such as other patients with pacer/ICDs. This will be described in greater detail below, particularly with reference to FIGS. 5-7. The default values also depend, of course, on the particular morphological parameters to be used and the particular abnormal physiological condition to be detected. Note though that, in some implementations, the detection thresholds need not be set in advance to specific default values. Rather, the thresholds may ultimately be passive. Also, the thresholds can include persistence-based thresholds, discussed below.

FIG. 3 illustrates various morphological parameters that may be derived from an IEGM signal and that may potentially be used to detect various abnormal physiological conditions within the patient. More specifically, FIG. 3 illustrates the primary morphological features of an intrinsic (i.e. un-paced) heartbeat 102, including the P-wave 104, QRS-complex 106 and T-wave 108 (all shown in stylized form.) Each of these primary features is characterized by various specific morphological parameters, such as width, peak amplitude, maximum slope, etc. Additionally, various intervals between individual features of the heartbeat may also be exploited, such as the atrioventricular (AV) interval between the P-wave and the QRS-complex, the ST segment interval between the end of the QRS-complex and the T-wave, and the aforementioned QTmax and QTend intervals. Also, as already explained, ST segment elevation can be exploited, as it is a particularly effective parameter for use in detecting cardiac ischemia. Most of the detection examples specifically described herein below employ ST segment elevation.

The precise morphological parameters to be employed in detecting abnormal conditions such as cardiac ischemia may be defined in any of a variety of various ways, depending upon the particular implementation, so long as one is consistent. For example, ST segment elevation may be defined relative to a baseline signal voltage, as shown, or relative to some fixed voltage, such as 0 V. The "P-wave width" may be defined as the interval between the very beginning and very end of the P-wave, as shown in FIG. 3. Alternatively, the width may be defined as a "full width/half maximum." In other examples, the width is defined as the interval between when the absolute magnitude of an atrial channel signal first exceeds an atrial channel sensing threshold (not shown) and when it subsequently falls below that sensing threshold. That is, any suitable definition of "P-wave width" may be employed so long as one is consistent. As another example, "maximum slope" may be defined as the maximum positive slope or the maximum negative slope. The AV interval may be defined, as shown, as extending between the beginning of the P-wave and the beginning of the QRS-complex. However, in other implementations, the AV interval is defined as the interval between when the P-wave is first detected based on the atrial channel sensing threshold and when the QRS-complex is detected based on a ventricular channel sensing threshold (not shown).

In the example of FIG. 3, a sensed (i.e. intrinsic) P-wave is shown along with a sensed (i.e. intrinsic) the QRS complex. Parameters may also be defined with respect to paced atrial and ventricular events. Furthermore, the particular parameters illustrated in FIG. 3 are merely exemplary. Other parameters that characterize aspects of the morphological features of the IEGMs may additionally or alternatively be used, depending upon the abnormal physiological condition to be detected. For example, the integral or sum of the area associated with a morphological feature may be detected, including a paced depolarization integral (PDI). Energy or frequency values associated with morphological features may be detected. Parameters associated with individual heartbeats are generally preferred as such parameters permit ischemia or other abnormal conditions to be detected substantially in real-time. However, depending upon the implementation, parameters associated with multiple heartbeats may additionally or alternatively be used. For example, intervals between features of consecutive heartbeats may be detected, such as R-R intervals and P-P intervals. In addition, R-R variability and P-P variability may be detected and exploited. Information pertaining to T-wave alternans may also be exploited, which are often associated within an electrophysiological instability in the patient. Otherwise routine experimentation may be employed to identify particular combinations of morphological parameters that are effective for detecting particular abnormal physiological conditions within the patient, at least those conditions that have an effect on IEGM morphology.

Returning to FIG. 2, at step 110, the pacer/ICD senses signals within the patient and derives values of the selected morphological parameters from the signals (such as ST segment elevations derived from an IEGM, contractility values derived from impedance measurements, or cardiac pressure values derived from a physiological sensor.) At step 112, the pacer/ICD monitors the values of the morphological parameter to detect a possible occurrence of the abnormal physiological condition by comparing the values to the default detection threshold or by any other suitable technique. For example, the amount of deviation in ST segment elevation may be compared at step 112 against a default ST segment deviation threshold and, if the amount of deviation exceeds that threshold, cardiac ischemia is thereby indicated. In one specific example, the default threshold is set to detect ischemia based on a 20% deviation from a mean ST segment elevation. Hence, any increase or decrease of the ST segment elevation from the mean ST segment elevation within a patient of more than 20% is deemed to be indicative of cardiac ischemia. Depending upon the implementation, ST segments derived from X out of Y heartbeats must meet this criterion for ischemia to be indicated (where, e.g., X is 7 and Y is 10) or X heartbeats within some predetermined interval of time.

As explained in the patent application of Gill et al., entitled "System and Method for Distinguishing among Ischemia, Hypoglycemia and Hyperglycemia Using an Implantable Medical Device," referenced above, hyperglycemia and hypoglycemia can also affect ST segment elevation. Accordingly, the pacer/ICD may also compare QTmax and QTend values derived from the IEGM against suitable thresholds so as to distinguish hyperglycemia and hypoglycemia from ischemia. Briefly, cardiac ischemia tends to shorten QTmax while leaving QTend substantially unchanged. Hypoglycemia typically causes both QTmax and QTend to lengthen; whereas hyperglycemia tends to cause little or nor change in either QTmax or QTend. The following table summarizes changes in the ST segment, QTmax and QTend in response to cardiac ischemia, hypoglycemia, hyperglycemia that may be exploited, as well as changes due to hyperkalemia and cardioactive drugs.

TABLE I

|  | ST Segment | QTmax | QTend |
|---|---|---|---|
| Ischemia | Significant deviation | Shortens | Little or no change |
| Hypoglycemia | Significant deviation | Lengthens | Lengthens |
| Hyperglycemia | Significant deviation | Little or no change | Little or no change |
| Hyperkalemia/ digitalis | Significant deviation | Shortens | Shortens |
| Normal/ cardioactive drugs (other than digitalis | No significant deviation | May vary with QTend | May vary with OTmax |

Insofar as normal variations in QTmax and QTend are concerned, under normal (i.e. non-ischemic, non-hypoglycemic, non-hyperglycemic and non-hyperkalemic) conditions, QT typically varies with heart rate, autonomic tone, cardioactive drugs, etc. However, under non-ischemic conditions, if QTmax and QTend vary, the two values typically change in lock-step, i.e. QTend-QTmax remains the same. The ST segment elevation does not change significantly under non-ischemic conditions. As shown, ST segment elevation does change due to ischemia, hypo/hyperglycemia, etc. However, the case where ST elevation changes, but QTend stays the same and QTmax shortens appears to be unique to ischemia and hence is useful for detecting ischemia and distinguishing it from other conditions.

As listed in Table I, hyperkalemia and the use of digitals can potentially affect QTmax. More specifically, they tend to shorten both QTmax and QTend. Hence, the techniques discussed herein can be used adjust detection thresholds relevant to possible hyperkalemia within the patient, as well. Still other conditions and/or medications can potentially affect QTmax and QTend as well. For example, left ventricular hypertrophy (LVH), left bundle branch block (LBBB), benign early repolarization (BER), right bundle branch block (RBBB), left ventricular aneurysm, and acute pericarditis might have some affect on these parameters. Also, various medications can affect repolarization kinetics and hence can affect QTmax and QTend, though cardioactive drugs typically cause no significant deviation in either QTmax or QTend. Nevertheless, QTmax and QTend can be used to help corroborate detection of ischemia initially made based on ST segment deviation only. Techniques for detecting and discerning between electrocardiographic effects of cardioactive drugs are described in U.S. Pat. No. 7,142,911, to Boileau, et al. Those techniques may be used to identify changes, if any, within cardiac signals caused by medications, such that those changes can then be taken into account when detecting and distinguishing ischemia, hypoglycemia, hyperglycemia and hyperkalemia. Still further, at least some cardiological conditions that can potentially affect QTmax and QTend, such as LVH and BER, typically do not cause short-term changes in ST or T-wave parameters, and hence do not interfere with detection of ischemia, hypoglycemia, hyperglycemia and hyperkalemia based on relatively short-term variations in the ST or T-wave parameters, which is of primary importance. See, also, U.S. patent application Ser. No. 11/740,175, filed Apr. 25, 2007 of Mason et al., entitled "System and Method for Efficiently Distinguishing among Cardiac Ischemia, Hypoglycemia and Hyperglycemia using an Implantable Medical Device and an External System."

Thus, steps 100-112 operate to detect cardiac ischemia or other abnormal physiological conditions using one or more defaults thresholds. Steps 114 and 116 operate to adjust those thresholds to improve detection accuracy or to set the thresholds, if not already set. More specifically, at step 114, the pacer/ICD collects information representative of a range of variation in the selected morphological parameters within the patient. That is, the values of the selected morphological derived at step 110 are stored within the pacer/ICD for analysis. As will be explained, one or more histograms may be advantageously exploited to collect the data. In any case, at step 116, the pacer/ICD then adjusts the detection thresholds based on the information representative of the range of variation in the selected morphological parameters collected within the patient so as to improve detection accuracy. In one example, step 116 is performed only following completion of a post-implant learning period based on data collected during the learning period. In other implementations, step 116 is also performed periodically during the learning period. In either case, even after completion of the learning period, step 116 is also preferably performed within the patient, at least periodically, to respond to changes in variability with the patient to keep the thresholds set to optimal values. Also, circumstance may arise when it is appropriate to reinitialize the procedure by resetting the thresholds to default values such as if the values of the morphological parameter from which the abnormal physiological condition is detected (at step 112) remain at levels in consistent with the abnormal physiological condition. For example, if the ST segment is used to detect ischemia and the ST segment elevation remains shifted for days or weeks, such is probably not indicative of a true ischemia, but is probably due to changes in medications or other factors (including myocardial infarction). Hence, the pacer/ICD preferably repeats the adaptive adjustment procedures (of steps 110-116) after resetting the thresholds to their default values. Appropriate diagnostic information indicating the reinitialization procedure may be stored in memory indicating, e.g., the cause of the reinitialization. Warnings might also be generated to notify the physician of the need to reinitialize the procedure.

FIG. 4 illustrates a range of deviation within ST segment elevation with a pair of patients and also illustrates the corresponding adjustments in detection thresholds that may be performed by the pacer/ICD at step 116 in response thereto. It should be noted that the graphs of FIG. 4 do not illustrate actual clinically-obtained data but instead illustrate hypothetical "stylized" data intended to clearly illustrate the principles of the invention. A first graph 118 illustrates ST segment elevation deviation over time in a patient in which relatively little deviation occurs, even during an episode of ischemia. As can be seen, the ST segment elevation 120 does not deviate much from the mean ST segment elevation of the patient until ischemia occurs, then there is a relatively modest increase. With detection thresholds set to default values of ±20%, the pacer/ICD does not detect the episode of ischemia. In other words, for this particular patient, the default threshold values initially set at step 100 of FIG. 2 are too broad. At step 116, however, the detection thresholds are adjusted based on the actual amount of deviation in ST segment elevation observed within the patient. In this particular example, an upper detection threshold (representative of a deviation in ST segment elevation above the mean) is reset to +5%, as shown by graph 122. A lower threshold (representative of a deviation in ST segment elevation below the mean) is reset to −5%. As such, additional episodes of ischemia that might otherwise be undetected using the default values would be properly detected. Note that the thresholds need not be symmetric, i.e., the upper and lower thresholds may be adjusted independently.

A third graph 124 illustrates ST segment elevation deviation over time in a different patient, one in which a significant amount of deviation occurs, even in the absence of ischemia. As can be seen, the ST segment elevation 126 deviates significantly, even in the absence of ischemia, perhaps due to patient activity, posture, or other factors. When an episode of ischemia occurs, there is an even greater amount of deviation. With detection thresholds set to default values of ±20%, the pacer/ICD generates several false alarms, particularly at times 128 and 130. In other words, for this particular patient, the default threshold values initially set at step 100 of FIG. 2 are too narrow. At step 116, the detection thresholds are adjusted based on the actual amount of deviation in ST segment elevation observed within the patient and, in this particular example, the upper detection threshold and the lower detection threshold are reset to ±25%, respectively, as shown by graph 132. As such, false alarms are eliminated (or at least greatly reduced), whereas actual episodes of ischemia are still detected.

ST Segment-Based Threshold Adjustment Example

Figure 5:
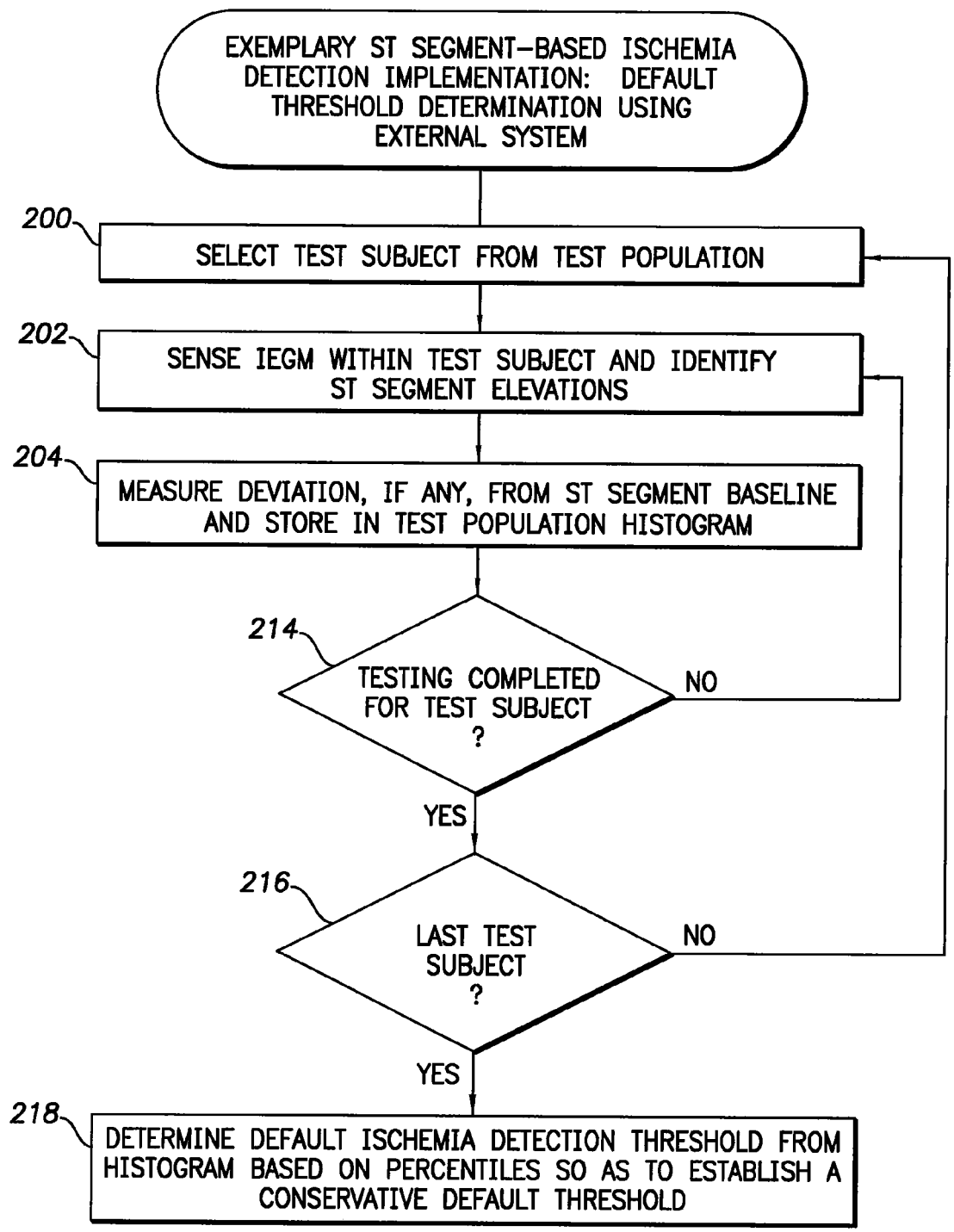
FIG. 5 is a flow diagram illustrating an exemplary pre-implant setup technique for determining a default ST segment-based ischemia detection threshold from a population of test subjects, which may be performed by an external system to determining defaults thresholds for use by the implantable system of FIG. 1.
Figure 6:
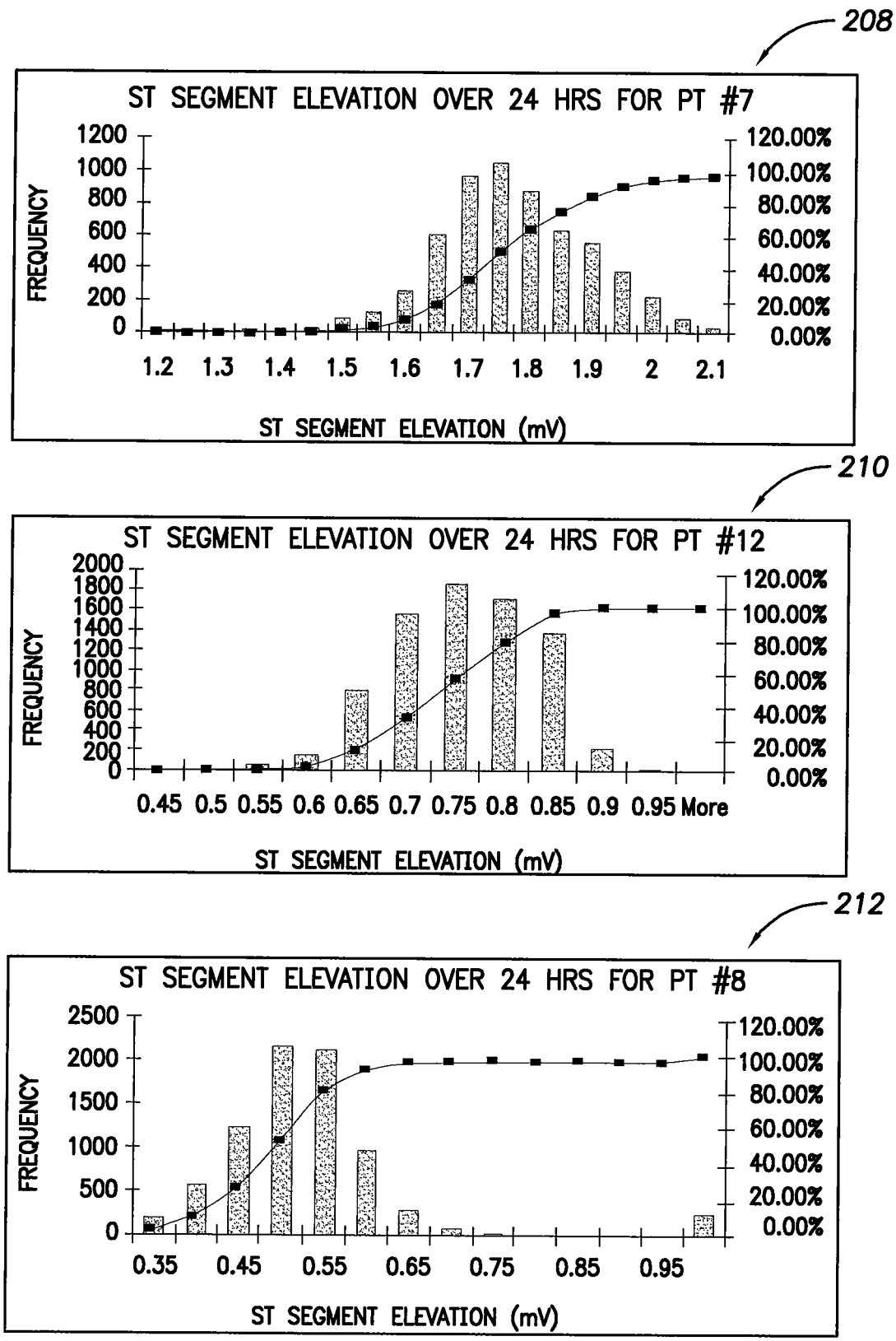
FIG. 6 sets forth exemplary histograms illustrating variations in ST segment elevation within three different test subjects, the data from which may be processed using the determination technique of FIG. 5.
Figure 7:
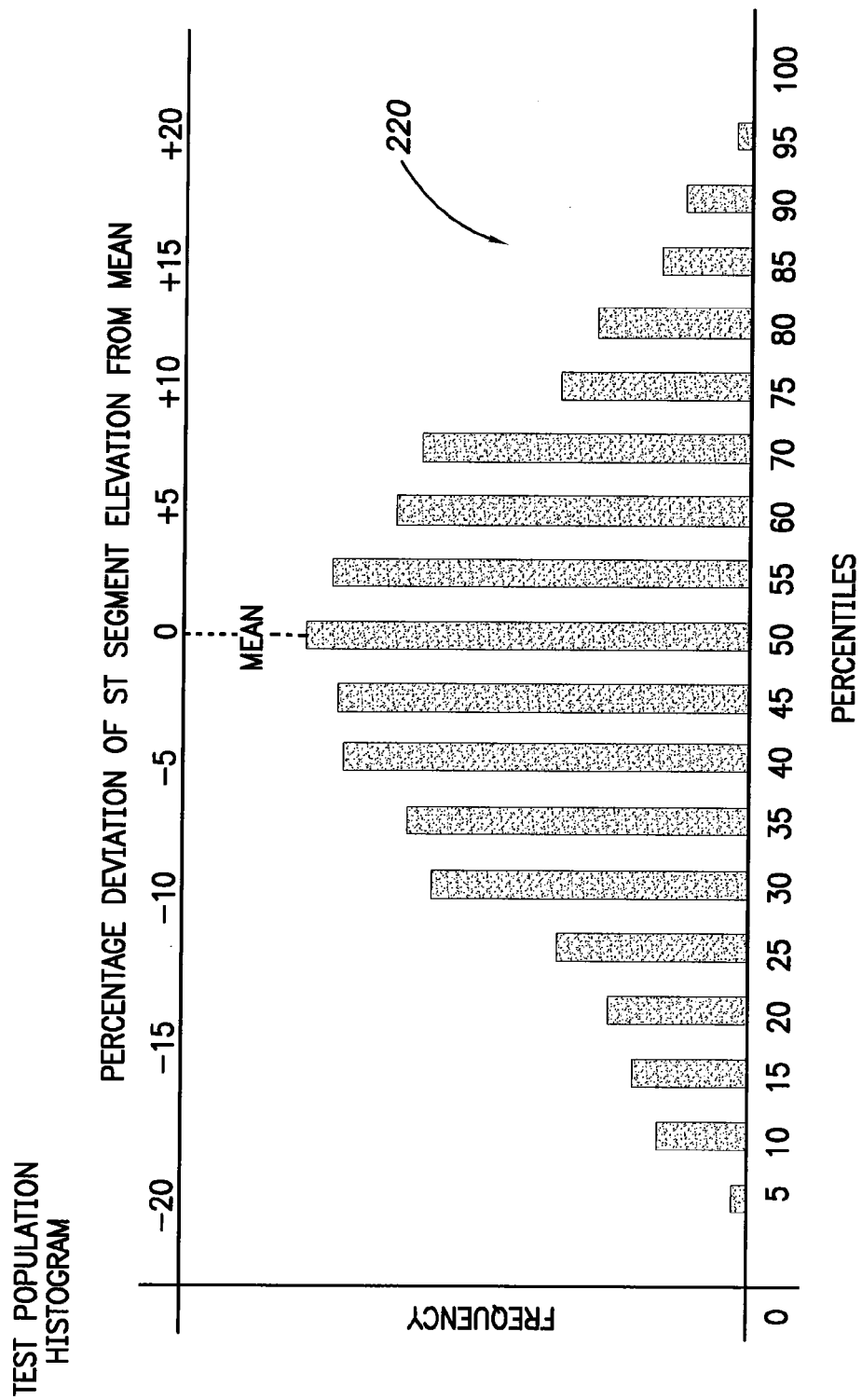
FIG. 7 sets forth a single exemplary combined histogram illustrating variations in ST segment elevation throughout a population of test subjects from which default ST segment-based thresholds may be determined using the techniques of FIG. 5.
Figure 8:
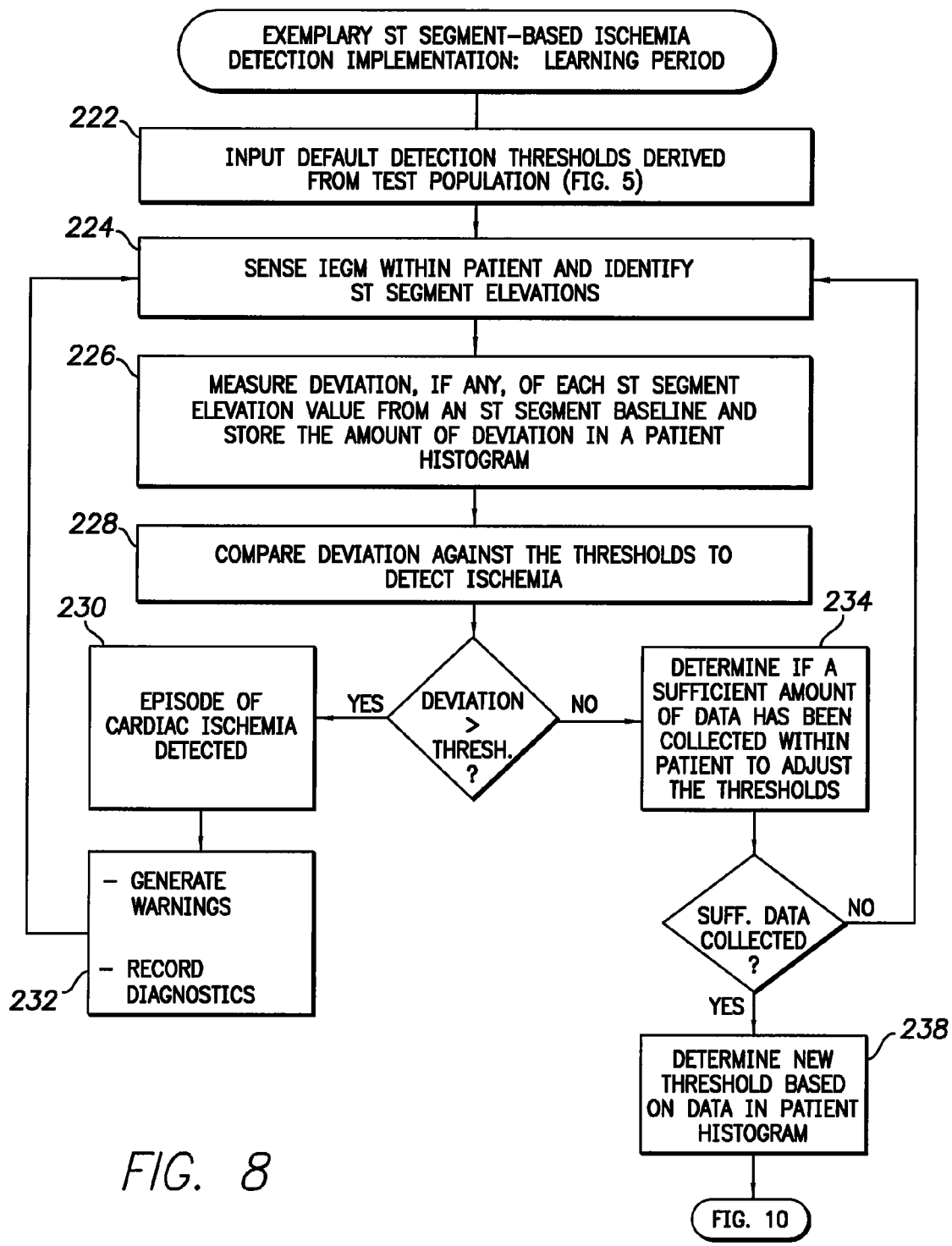
FIG. 8 is a flow diagram illustrating an exemplary learning technique for use by the implantable system of FIG. 1 to collect data to use to adjust the ST segment-based thresholds initially determined by the pre-implant setup technique of FIG. 5.
Figure 9:
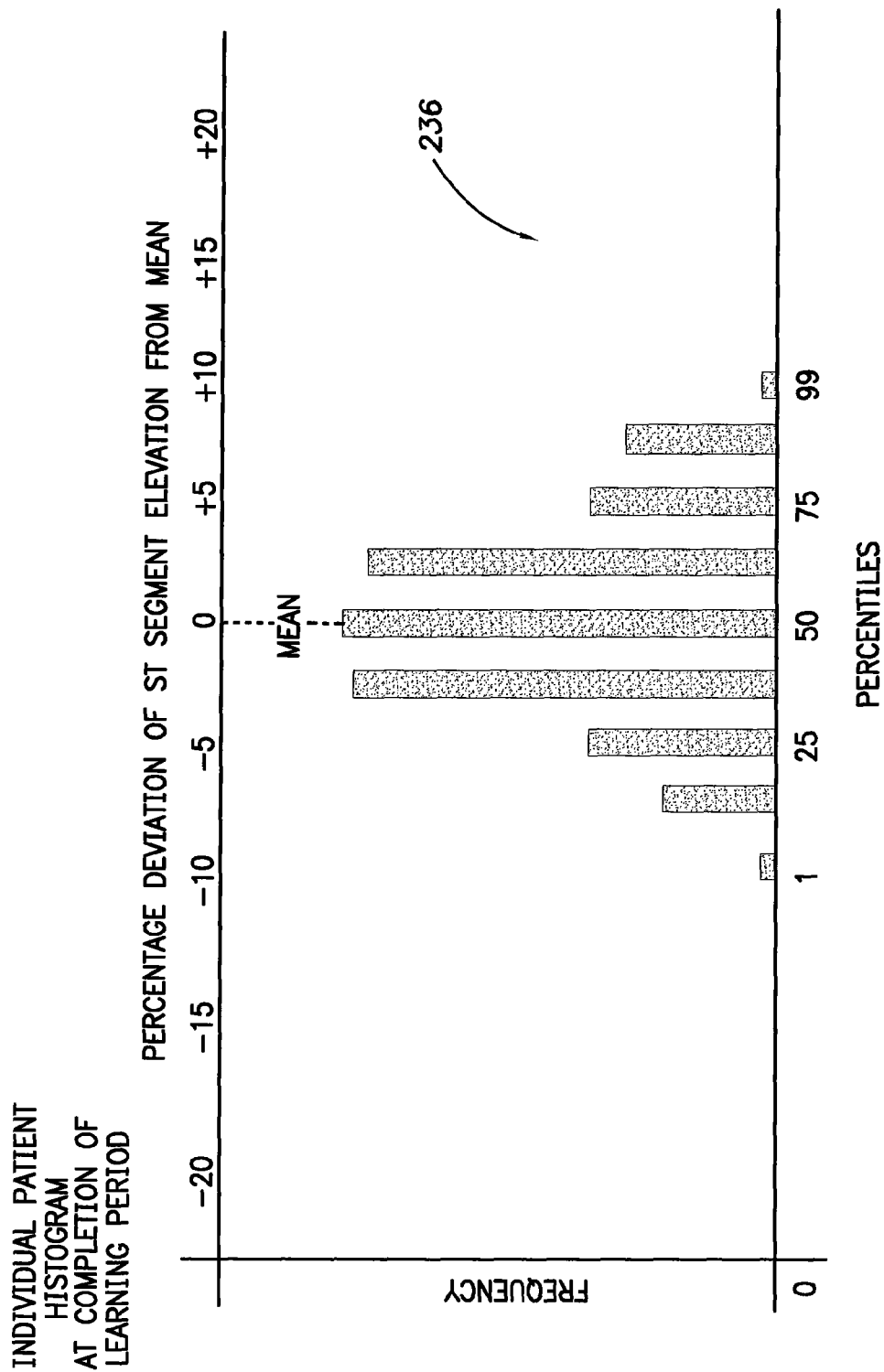
FIG. 9 sets forth a single exemplary histogram illustrating variations in ST segment elevation within an individual, exemplary patient from which new ST segment-based thresholds may be determined using the techniques of FIG. 8.
Figure 10:
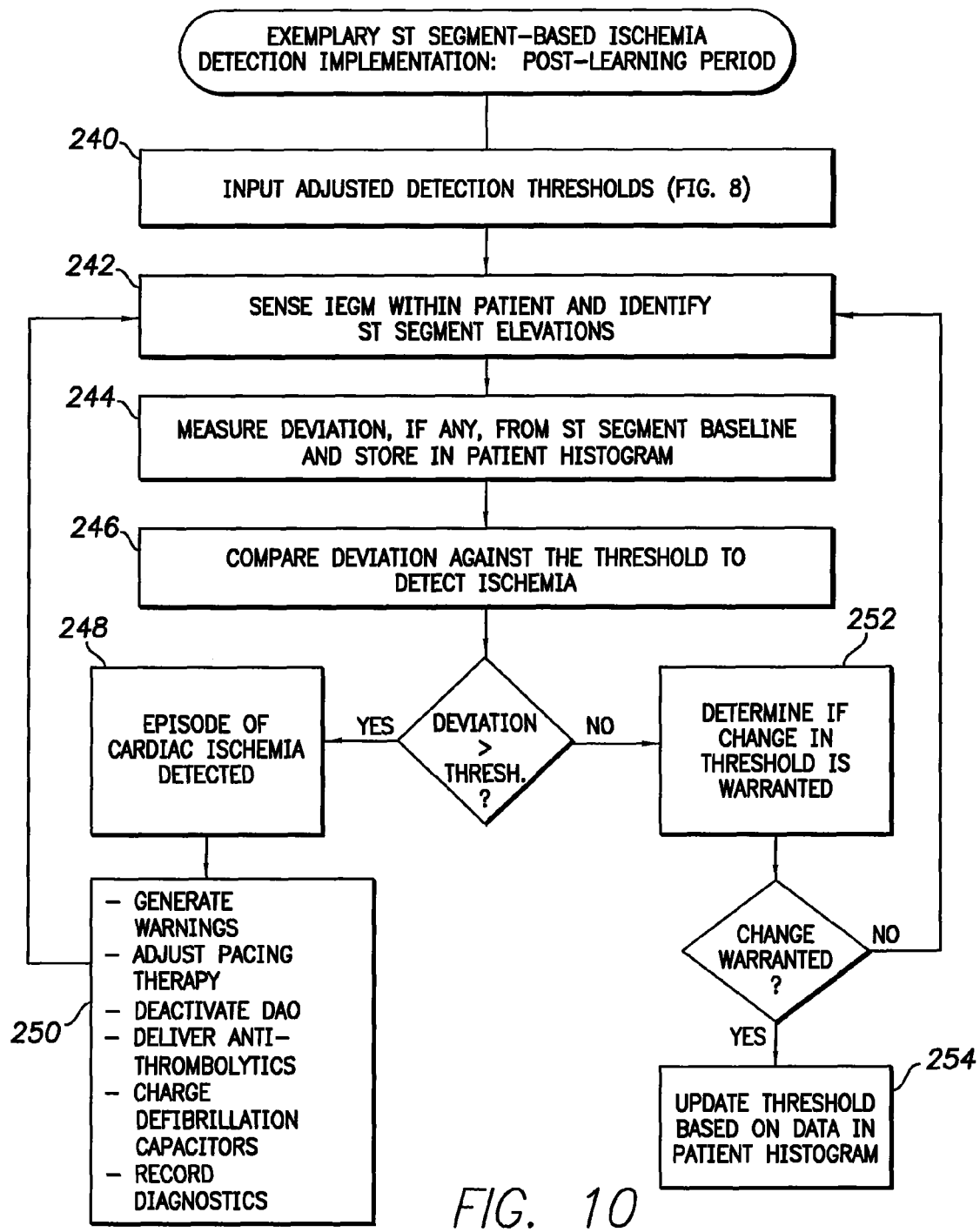
FIG. 10 is a flow diagram illustrating an exemplary post-learning technique for use by the implantable system of FIG. 1, wherein the adjusted ST segment-based thresholds determined by the technique of FIG. 8 are exploited.

Turning now to FIGS. 5-10, an exemplary technique exploiting ST segment elevation will be described in greater detail. FIGS. 5-7 illustrate pre-implant techniques performed in conjunction with an external system to determine default threshold values based on a degree of variability observed in a population of test subjects. FIGS. 8-9 illustrate the learning procedure performed by an exemplary pacer/ICD following implant within a patient to adjust and adapt the default thresholds based on the degree of variability in detection parameters observed in the patient. FIG. 10 illustrates the continued operation of the pacer/ICD using the adjusted thresholds following the learning period.

At step 200 of FIG. 5, a test subject is selected from a population of test subjects and, at step 202, IEGMs are sensed within the test subject and ST segment elevations are derived. The test subject may be, for example, a patient in whom a pacer/ICD has already been implanted. At step 204, the deviation, if any, from an ST segment baseline value is calculated and stored in test population histogram, with different bins for different ranges of ST segment deviation, both above and below the baseline. The bins may be implemented as counters in software. The baseline may be, e.g., a mean ST segment elevation voltage within the particular test subject. Steps 202-204 are repeated over a period time (such as twenty-four hours) during which the patient is not subject to ischemia (as verified, e.g., using a conventional ischemia detection technique employing a Holter monitor or the like) to populate the patient histogram with a statistically sufficient amount of data.

Once a sufficient amount of data has been collected from the particular test subject selected at step 200, as determined at decision block 214, steps 200-204 are then repeated for another test subject to obtain data for that test subject. Preferably, data from a sufficiently large number of test subjects is obtained in this manner is collect a statistically significant amount of data from which viable default threshold values may be determined. Once data for the last test subject has been collected, as determined at decision block 216, the external system then determines, at step 218, default ischemia detection thresholds from the test subject histograms based on, e.g. predetermined percentiles so as to establish conservative default thresholds. To this end, the external system may combine the data from the individual test subject histograms into a single test population histogram.

FIG. 6 illustrates a set of exemplary patient histograms 208, 210, 212 obtained from three test subjects, with the data collected over twenty-four hour periods. FIG. 7 illustrates an exemplary test population histogram 220 with data collected in various percentile bins. The test population histogram is examined to determine appropriate "conservative" upper and lower thresholds. In one example, the external system determines the percentage deviation from the baseline corresponding to predetermined percentile values, such as the 5th percentile and 95th percentile. In other words, the lower threshold is set to whatever percentage deviation value corresponds to the 5th percentile of the test population histogram (such as, e.g., −20%); whereas the upper threshold is set to whatever percentage deviation value corresponds to the 95th percentile of the test population histogram (such as, e.g., +20%). The percentiles need not be symmetric. Also, note that the histogram of FIG. 7 does not illustrate actual clinically-obtained data but instead illustrates hypothetical test subject population data intended to clearly illustrate the principles of the invention.

The default threshold values determined by the technique of FIGS. 5-7 are then programmed into the memory of a pacer/ICD for implant within a patient. FIGS. 8-10 summarize operations performed by the implanted device during its learning period when it uses the default threshold values to detect ischemia while collecting patient data for use in subsequently adjusting the thresholds. At step 222 of FIG. 8, the pacer/ICD inputs the default detection thresholds from memory and, at step 224, begins sensing IEGM signals within patient and identifying individual ST segment elevations. If not already done, the pacer/ICD also determines a baseline value for the ST segment elevations, such as its mean. At step 226, the pacer/ICD measures the deviation, if any, of each individual ST segment from the baseline and stores that deviation value in a patient histogram for subsequent use in adjusting the thresholds. At step 228, the pacer/ICD compares the deviation against the upper and lower default thresholds to detect ischemia. If the deviation exceeds the default thresholds, an episode of ischemia is thereby detected, at step 230, and appropriate warning signals are triggered, at step 232.

In this example, no therapies are automatically delivered, in view of the possibility of false alarms arising due to the use of the default thresholds. As already noted, depending upon the programming of the device, some predetermined number of ST segment deviations must exceed the threshold, such as X out of Y, for ischemia to be indicated. Alternatively, some predetermined number of segment deviations must exceed the threshold over a predetermined interval of time, such as over a period of one minute. Still other detection criteria may be used. At step 232, the pacer/ICD also records diagnostic information for subsequent physician review, including recorded IEGMs for the particular sequence of heartbeats that triggered the ischemia warning, as well as the date/time of the detection of the episode of ischemia, the duration of the episode, and the particular pacing parameters employed by the pacer/ICD at that time. If however, the ST segment deviation remained within the default thresholds, then step 234 is instead performed where the pacer/ICD determines if a sufficient amount of ST segment elevation data has been collected within the patient to warrant adjusting the threshold values.

As noted in the Summary, multiple thresholds may be exploited for use with the same morphological parameter, which take into account persistence. For example, upper and lower ST segment deviation thresholds may be defined. If the ST segment deviation exceeds the upper ST-based threshold, ischemia is thereby detected, even if the ST segment remains elevated for only a relatively short period of time, such as one minute. However, if the ST segment deviation only exceeds the lower ST-based threshold, ischemia is thereby detected only if the deviation persists over some longer period of time, such as fifteen minutes. That is, a relatively mild ischemia is detected only if it is persistent. A more severe ischemia is detected based solely on the amount of ST segment deviation. In other examples, mild ischemia is detected whenever the ST segment deviation exceeds the lower threshold. The mild ischemia is reclassified as severe if it persists for more than fifteen minutes. As can be appreciated, the techniques described herein apply to these and other variations on threshold-based detection procedures.

FIG. 9 illustrates an exemplary patient histogram for use in collecting patient data at step 226. Patient histogram 236 includes bins for various ranges of percentage deviations, above and below the baseline mean. In one example, the pacer/ICD determines (at step 234 of FIG. 8) whether a sufficient amount of data has been collected by determining whether the histogram has been adequately populated with data. Otherwise conventional statistical techniques may be used in this regard. Assuming the histogram has been adequately populated with data, then the pacer/ICD, at step 238 of FIG. 8, determines new detection thresholds based on the data in the patient histogram. The same general techniques initially used by the external system to set the default threshold values based on the test population histogram may be used to set new threshold values for the patient based on the patient histogram. In the particular example of FIG. 9, the pacer/ICD, resets the upper threshold to correspond to a 5% increase in ST segment elevation relative to the baseline, and resets the lower threshold to correspond to a 5% decrease in ST segment elevation relative to the baseline, as there are relatively few counts within the bins beyond those ranges. Percentiles may be used to identify the appropriate thresholds for use with the particular patient. In one example, the pacer/ICD sets the new thresholds based on the 1st and 99th percentiles of the data collected within the patient histogram, thus making the new detection thresholds considerably less conservative than the default thresholds.

Once the thresholds have been adjusted, the learning period is complete and further processing proceeds in accordance with FIG. 10. The post-learning processing of FIG. 10 is similar to that of the learning period, but using the newly adjusted thresholds. Accordingly, only pertinent differences will be described in detail. At step 240, the pacer/ICD inputs the newly adjusted threshold values and then, at steps 242-246, detects new ST segment elevations, measures their deviations from the baseline, and compares those deviations to the new thresholds to detect ischemia. Additionally, the device continues to collect data within the patient histogram so as to permit the thresholds to be adjusted again, if needed. (Preferably, any data obtained during a period of time wherein the patient is deemed to be ischemic is not stored within the histogram so that such data does not skew the histogram.) If ischemia is detected using the adjusted thresholds, step 248, then warnings are delivered and appropriate therapies are also initiated, at step 250, depending upon the programming and capabilities of the device. More specifically, the pacer/ICD may be programmed to (1) generate warnings; (2) adjust pacing therapy; (3) deactivate dynamic atrial overdrive (DAO) pacing (if it is currently being applied); (4) deliver anti-thrombolytics or other appropriate medications via a drug pump; (5) charge defibrillation capacitors (if the pacer/ICD is equipped to deliver defibrillation shocks). Adjustments to pacing therapy in response to cardiac ischemia may involve, for example, reduction of a base pacing rate so as to prevent a relatively high programmed base rate from exacerbating the ischemia. DAO is preferably deactivated, again to prevent exacerbation of the ischemia. DAO is described in U.S. Pat. No. 6,519,493 to Florio et al., entitled "Methods and Apparatus for Overdrive Pacing Heart Tissue Using an Implantable Cardiac Stimulation Device." Anti-thrombolytics or other medications are preferably delivered using an implanted drug pump, if one is provided. The aforementioned patent to Lord et al. also discusses implantable drug pumps. Routine experimentation may be employed to identify medications for treatment of cardiac ischemia that are safe and effective for use in connection with an implantable drug pump. Also, as before, diagnostics data is recorded for subsequent physician review.

In some implementations, prior to delivering therapy or generating warnings, the pacer/ICD corroborates the detection of ischemia using other ischemia detection techniques. See, for example, the techniques described in the Ke at al., patent application cited above, entitled "Ischemia Detection using T-wave Amplitude, QTmax and ST Segment Elevation and Pattern Classification Techniques." See also, the Wang at al. patent application cited above, entitled "System and Method for Detecting Cardiac Ischemia Using an Implantable Medical Device." Another technique for detecting cardiac ischemia based on T-waves is set forth in U.S. patent application Ser. No. 10/603,398, entitled "System And Method For Detecting Cardiac Ischemia Based On T-Waves Using An Implantable Medical Device", of Min et al., filed Jun. 24, 2003. With the technique of Min et al., cardiac ischemia is detected based either on the total energy of the T-wave or on the maximum slope of the T-wave.

If however, the ST segment deviation remained within the adjusted thresholds, then step 252 is instead performed where the pacer/ICD determines if a further adjustment in the threshold values is warranted. In one example, the pacer/ICD determines (at step 252) whether a sufficient amount of change has occurred in the shape of the histogram to warrant adjusting the thresholds. For example, the amount of variability in ST segment elevations may have decreased within the patient, perhaps due to changes in lifestyle, newly prescribed medications, or progression or regression of cardiovascular diseases. Otherwise conventional statistical techniques may be used in this regard to assess changes in the histogram and determine whether those changes warrant an adjustment to the thresholds. Assuming that an adjustment is warranted, then the pacer/ICD, at step 254, determines new detection thresholds based on the data in the current patient histogram. Percentiles may again be used to identify the appropriate thresholds for use with the particular patient. For example, the pacer/ICD may adjust the thresholds to again correspond to the 1st and 99th percentiles of the data within the new patient histogram.

Multi-Parameter Threshold Adjustment Example

Figure 11:
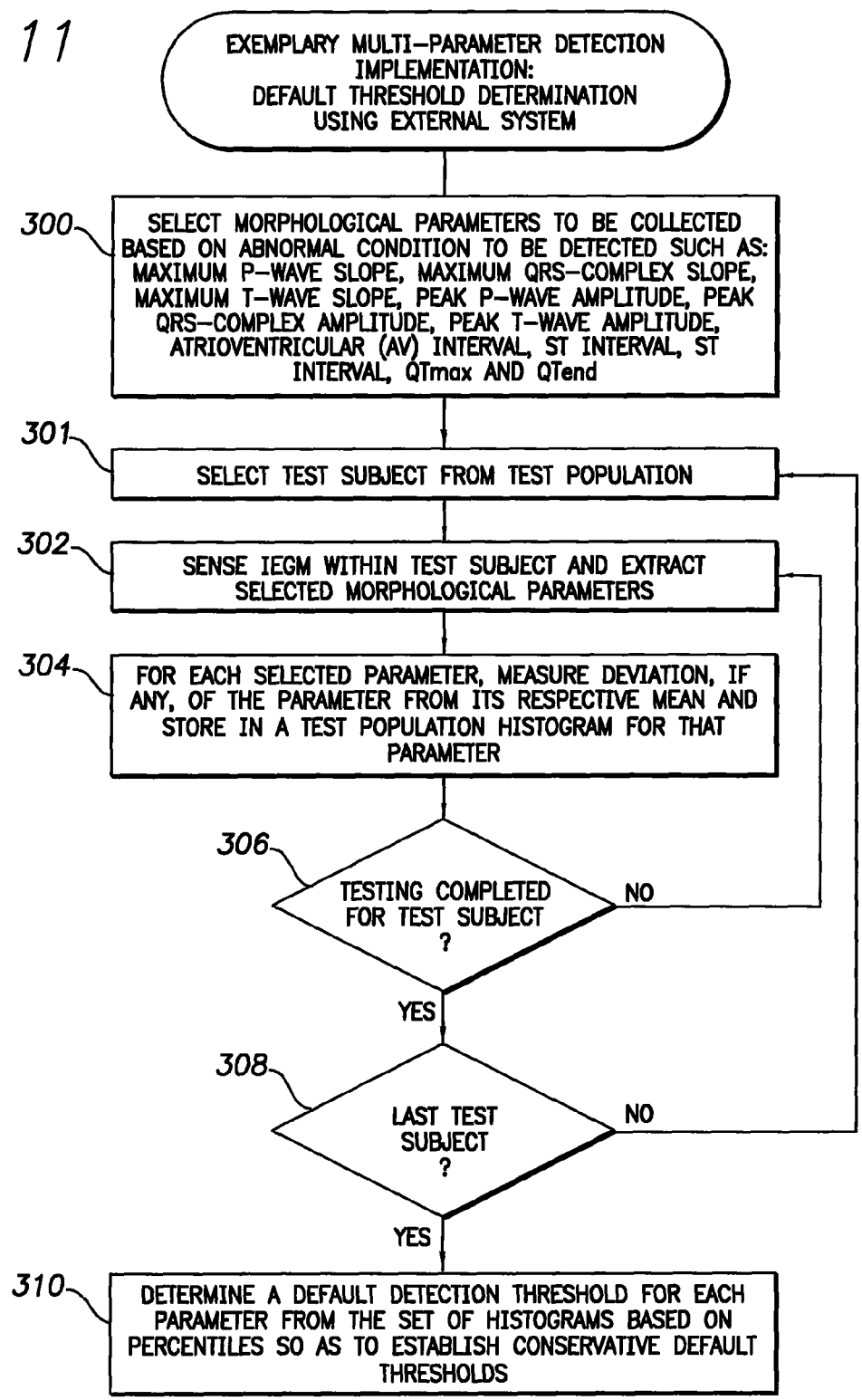
FIG. 11 is a flow diagram illustrating an exemplary multi-parameter pre-implant technique for determining an entire set of default detection thresholds from a population of test subjects for use with a set of morphological parameters, which may be performed by an external system to determine a set of initial thresholds for use by the implantable system of FIG. 1.
Figure 12:
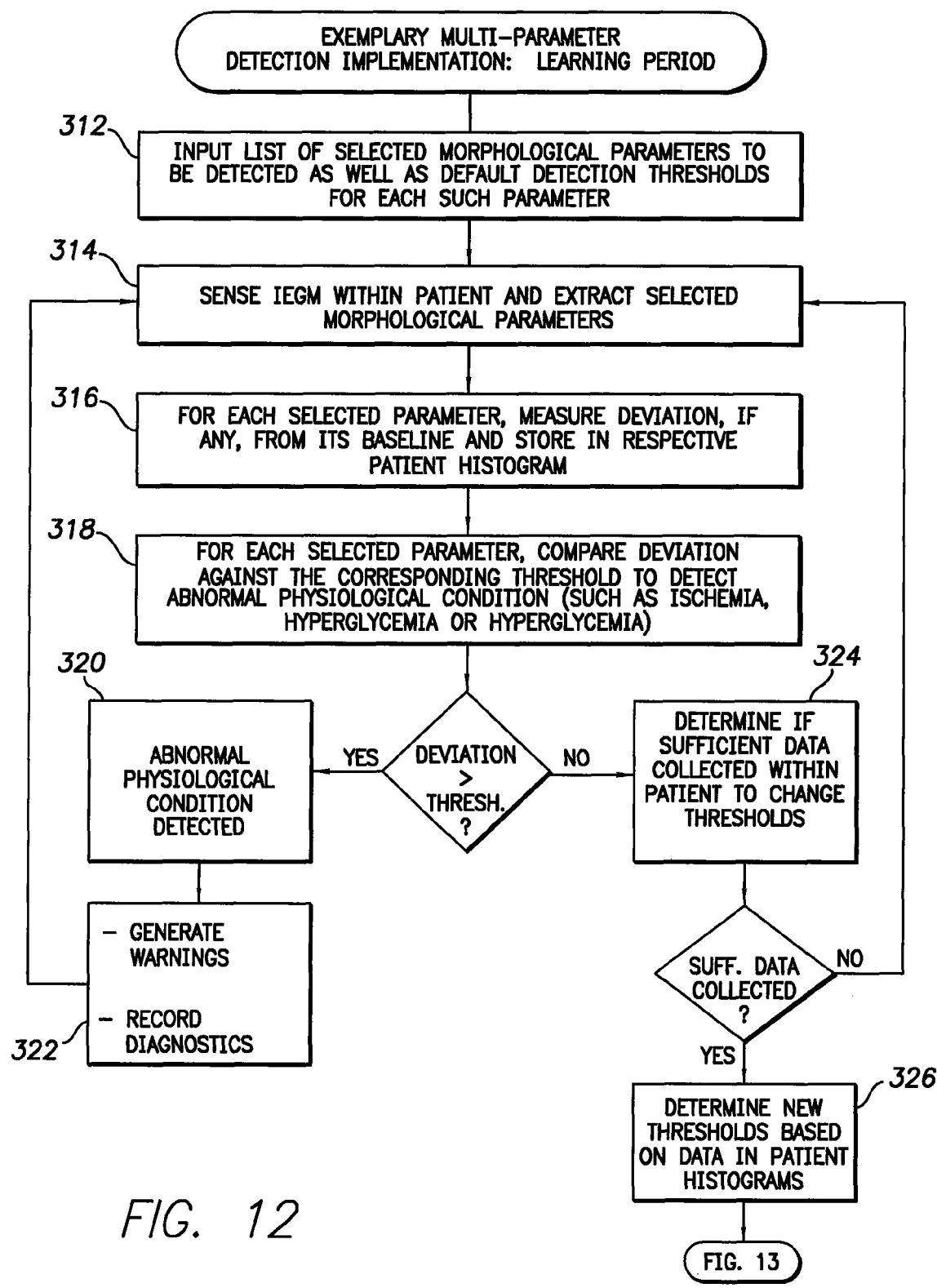
FIG. 12 is a flow diagram illustrating an exemplary multi-parameter learning technique for use by the implantable system of FIG. 1 to collect data to use to subsequently adjust any of the set of default thresholds initially determined using the pre-implant setup technique of FIG. 11.
Figure 13:
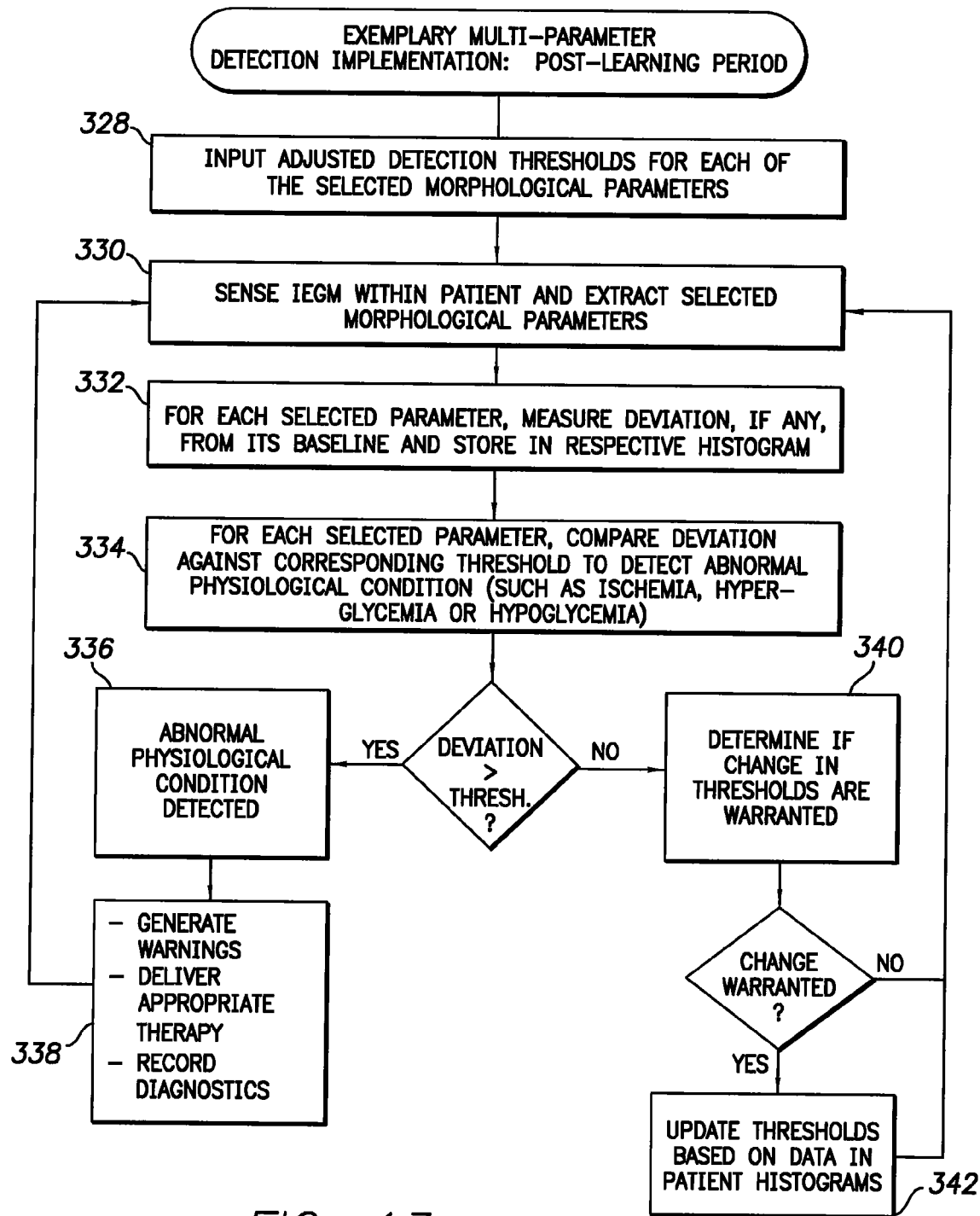
FIG. 13 is a flow diagram illustrating an exemplary multi-parameter post-learning technique for use by the implantable system of FIG. 1, wherein one or more of the adjusted thresholds determined by the technique of FIG. 12 are exploited.

FIGS. 11-13 illustrate an implementation where multiple morphological parameters are tracked for use in detecting one or more abnormal medical conditions, such as ischemia, hyperglycemia and/or hypoglycemia. Many of the steps are similar to those of FIGS. 5, 8 and 10 and only pertinent differences will be described in any detail. At step 300 of FIG. 11, various morphological parameters are selected depending upon the particular abnormal physiological condition to be detected. Examples include: maximum P-wave slope, maximum QRS-complex slope, maximum T-wave slope, peak P-wave amplitude, peak QRS-complex amplitude, peak T-wave amplitude, AV interval, ST interval, QTmax and QTend. For a given abnormal condition, the particular parameters to be selected are those parameters that are significantly affected by the onset of the condition, which may be determined by, e.g., routine experimentation. At step 301, a test subject is selected from a population of test subjects and, at step 302, IEGMs are sensed within the test subject and the selected morphological parameters are extracted from the IEGMs. At step 304, for each selected parameter, the deviation if any from a corresponding baseline value is calculated and stored in a cell of a test population histogram, with different bins for different morphological parameters and for different ranges of deviation of the parameters from their respective baseline values. Each baseline may be, e.g., a mean value of that particular parameter within that particular test subject. Steps 302-304 are repeated over a period time (such as twenty-four hours) during which the patient is not subject to the abnormal condition to be detected (as verified, e.g., using a conventional detection technique) to populate the patient histogram with a statistically sufficient amount of data for each of the morphological parameters originally selected at step 300.

Once a sufficient amount of data has been collected from the particular test subject selected at step 301, as determined at decision block 306, steps 302-304 are then repeated for another test subject to obtain data for that test subject. Preferably, data from a sufficiently large number of test subjects is obtained in this manner to collect a statistically significant amount of data from which viable default threshold values may be determined for each of the selected morphological parameters. Once sufficient data for the last test subject has been collected, as determined at decision block 308, the external system then determines, at step 310, default detection thresholds for each of the selected morphological parameters from the test subject population histogram based on, e.g. predetermined percentiles so as to establish conservative default thresholds for each parameter. To this end, the external system may combine the data from the individual test subject histograms into a single test population histogram. In one example, the external system determines, for each morphological parameter, the percentage deviation from the respective baseline corresponding to predetermined percentile values, such as the 5th percentile and 95th percentile. The percentiles may differ from one morphological parameter to another and, even for a given morphological parameter, the upper and lower percentiles need not be symmetric. The procedure of FIG. 11 may be repeated as needed, to generate different thresholds for detecting different abnormal physiological conditions. In some cases, the same morphological parameters may be used, but with different threshold values specified for the different abnormal conditions.

The default threshold values determined by the technique of FIG. 11 are then programmed into the memory of a pacer/ICD for implant within a patient. FIGS. 12-13 summarizes operations performed by the implanted device during its learning period when it uses the default threshold values to detect the abnormal physiological condition while collecting patient data for use in subsequently adjusting the thresholds. At step 312 of FIG. 12, the pacer/ICD inputs the list of selected morphological parameters to be used to detect the abnormal physiological condition of interest, as well as the default detection thresholds for those parameters from memory and, at step 314, begins sensing IEGM signals within patient and extracting the selected morphological parameters. If not already done, the pacer/ICD also determines baseline values for each of the morphological parameters for the patient, such as respective mean values. At step 316, for each of the selected morphological parameters, the pacer/ICD measures the deviation, if any, of each individual instance of that morphological parameter from its respective baseline and stores that deviation value in a corresponding cell of the patient histogram for subsequent use in adjusting the thresholds. At step 318, the pacer/ICD compares, again for each selected morphological parameter, the deviations against the respective thresholds to detect the abnormal physiological condition. If the deviation of each of the selected morphological parameters exceeds its respective threshold, an episode of the abnormal condition is thereby detected, at step 320, and appropriate warning signals are triggered, at step 322, which will depend on the particular abnormal condition. At step 322, the pacer/ICD also records diagnostic information for subsequent physician review, including recorded IEGMs for the particular sequence of heartbeats that triggered the warning, as well as the date/time of the detection of the episode of the abnormal condition, the duration of the episode, and the particular pacing parameters employed by the pacer/ICD at that time.

If however, the deviation values of each of the selected morphological parameters remained within their default thresholds, then step 324 is instead performed where the pacer/ICD determines if a sufficient amount of data has been collected within the patient to warrant adjusting the threshold values for any or all of the morphological parameters. In one example, the pacer/ICD determines whether a sufficient amount of data has been collected for a particular morphological parameter by determining whether the portion of the patient histogram corresponding to that morphological parameter has been adequately populated with data. Assuming the histogram has been adequately populated with data for each of the selected morphological parameters, then the pacer/ICD, at step 326, determines new detection thresholds for each of the morphological parameters based on the data in the patient histogram. The same general techniques initially used by the external system to set the default threshold values based on the test population histogram may be used to set new threshold values for the patient based on the patient histogram. Preferably, the new detection thresholds are set so as to be considerably less conservative than the default thresholds.

Once the set of thresholds has been adjusted, the learning period is complete, and processing proceeds in accordance with FIG. 13. The post-learning processing of FIG. 13 is similar to that of the learning period of FIG. 12, but using the newly adjusted thresholds. At step 328, the pacer/ICD inputs the adjusted detection thresholds for each of the selected morphological parameters used to detect the abnormal physiological condition from memory and, at step 330, begins sensing IEGM signals within patient and extracting the selected morphological parameters. At steps 332-334, the pacer/ICD detects new values of the selected morphological parameters, measures their deviations from the baseline, and compares those deviations to the new thresholds to detect the abnormal condition. Additionally, the device continues to collect data within the patient histogram so as to permit the thresholds to be adjusted again, if needed. (Preferably, any data obtained during a period of time wherein the patient is deemed to have the abnormal condition is not stored within the histogram so that such data does not skew the histogram.)

If the abnormal condition is detected using the adjusted thresholds, step 336, then warnings are delivered and appropriate therapies are also initiated, at step 338, depending upon the abnormal conditions detected, the device programming and the capabilities of the device. Also, as before, diagnostics data is recorded for subsequent physician review. In some implementations, prior to delivering therapy or generating warnings, the pacer/ICD corroborates the detection of the condition using other detection techniques. If however, the various deviation values remained within their adjusted thresholds, then step 340 is instead performed where the pacer/ICD determines if a further adjustment in the threshold values is warranted. In one example, the pacer/ICD determines whether a sufficient amount of change has occurred in the shape of one or more of the histograms corresponding to the selected morphological parameters to warrant adjusting the thresholds for those parameters. Assuming that an adjustment is warranted, then the pacer/ICD, at step 342, determines new detection thresholds based on the data in the current patient histograms. Percentiles may again be used to identify the appropriate thresholds for use with the particular patient.

Condition-Specific Threshold Detection Example

Figure 14:
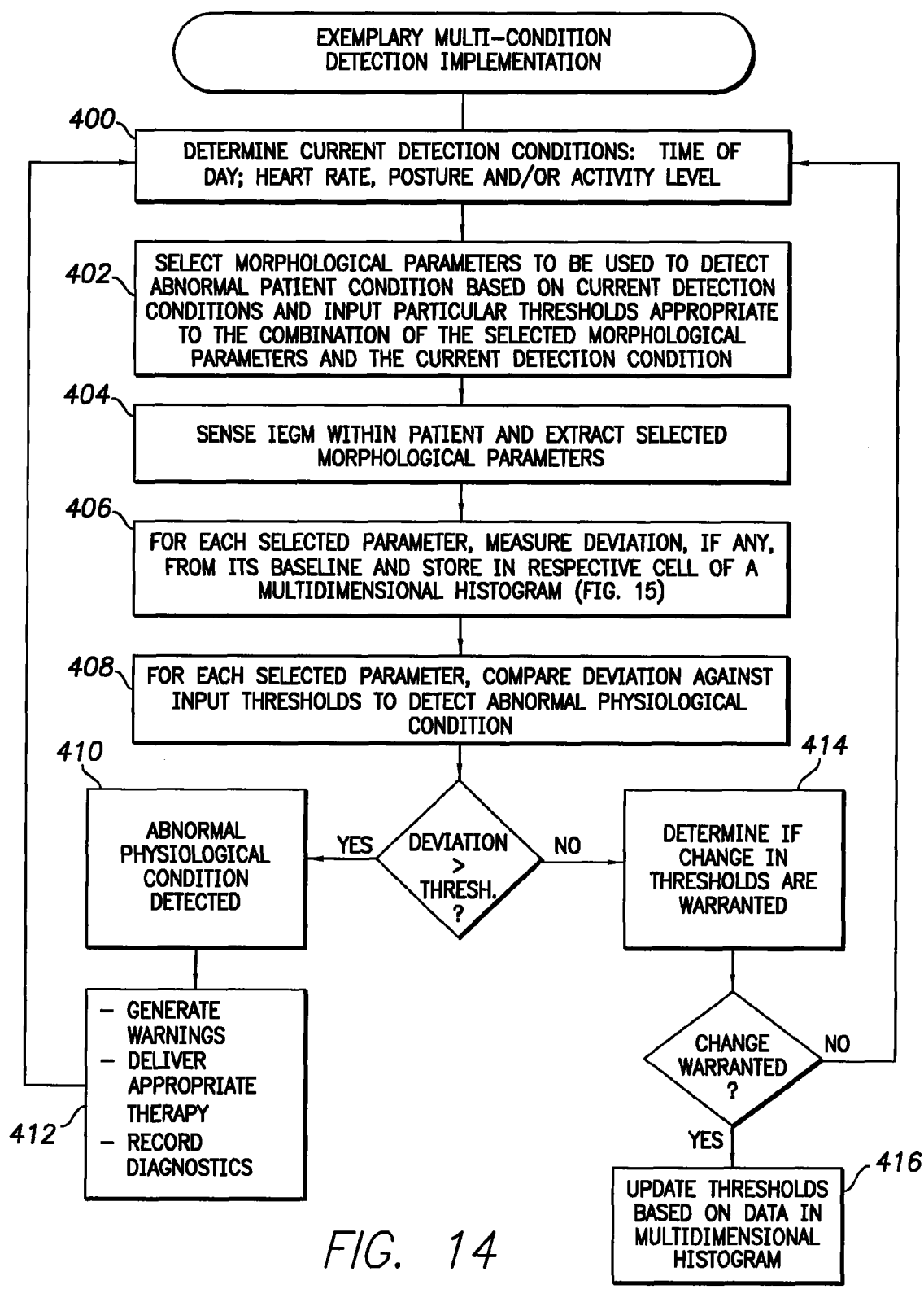
FIG. 14 is a flow diagram illustrating an exemplary condition-specific detection technique for use by the implantable system of FIG. 1, wherein condition-specific thresholds are employed such as thresholds specific to patient activity levels, time or day or patient posture.
Figure 15:
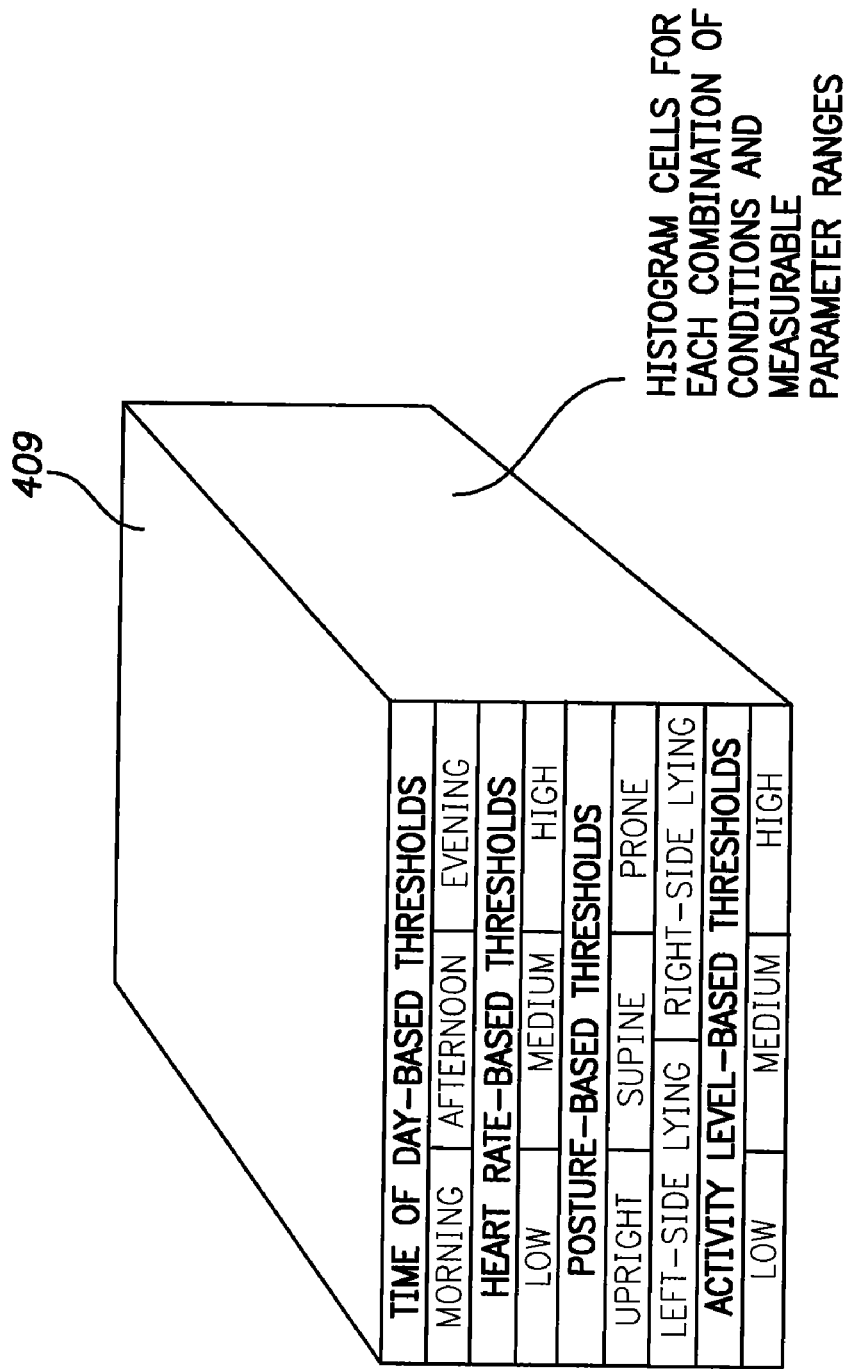
FIG. 15 is a diagram illustrating an exemplary multi-dimensional histogram that may be exploited in connection with the technique of FIG. 14, wherein separate thresholds are employed for separate conditions, such as time of day, heart rate, or posture.

FIGS. 14-15 illustrate an implementation where different thresholds are used that are specific to particular conditions within the patient such as heart rate, activity level, posture, time of day. This implementation also exploits multiple different morphological parameters for use in detecting various abnormal medical conditions, such as ischemia, hyperglycemia and/or hypoglycemia. Many of the steps, again, are similar to those already described and only pertinent differences will be described in any detail. At step 400 of FIG. 14, the pacer/ICD determines current detection conditions within the patient including one or more of: time of day, heart rate, posture and activity level. Time of day may be determined to identify, e.g., whether it is morning, afternoon, or evening/night. Heart rate may be categorized as high, medium or low. Activity level may likewise be categorized as high, medium or low. Activity levels may be detected using activity sensors or the like. Posture may be determined to identify one or more of: an upright posture threshold, a supine posture threshold, a prone posture threshold, a left-side lying posture threshold and a right-side lying posture threshold. Posture may be detected, for example, using techniques described in: U.S. patent application Ser. No. 10/329,233, of Koh et al., entitled "System and Method for Determining Patient Posture based on 3-D Trajectory Using an Implantable Medical Device," filed Dec. 23, 2002, or by using other suitable posture detection techniques.

At step 402, the pacer/ICD selects morphological parameters to be used to detect a particular abnormal patient condition (such as cardiac ischemia, hyperglycemia, and/or hypoglycemia) based on the current detection conditions. For example, depending upon the programming of the device, if the heart rate is high and the activity level is also high, the pacer/ICD may select one set of morphological parameters to detect the abnormal physiological condition; whereas a different set might be selected if the heart rate is high but the activity level is instead low. That is, in some implementations, a different set of morphological parameters are specified for each combination of patient conditions (as well as for each abnormal physiological condition to be detected). In other implementations, the same morphological parameters are used regardless of the current detection condition. At step 402, the pacer/ICD also inputs particular condition-specific thresholds appropriate to the combination of the selected morphological parameters and the current detection condition. Hence, for each morphological parameter to be compared against a detection threshold, there may be different thresholds depending upon the current detection condition within the patient. For example, if the morphological parameter to be used is ST segment elevation and the pacer/ICD tracks heart rate and activity levels, there may be one threshold for use with high heart rate and high activity level; a different threshold for high heart rate and low activity level; yet another different threshold for low heart rate and high activity level, etc. In this manner, a different threshold can be specified for use with each combination of detection conditions: time of day; heart rate, posture and activity level, as well as for different the morphological parameters and the different abnormal physiological conditions to be detected.

As can be appreciated, depending upon on the programming and capabilities of the device, hundred of different thresholds can be used, each independently adjustable by the pacer/ICD based on the amount of variability in the morphological parameters occurring within the patient during those conditions. Default values for the various thresholds can be determined in advance using the pre-implant techniques discussed above. The default thresholds values may then be adjusted based on patient data obtained during a learning period, as also described above. (FIG. 14 assumes that the default parameters have already been adjusted and illustrates their subsequent use within the patient to detect abnormal physiological conditions.) At step 404, the pacer/ICD senses the IEGM within patient and extracts the selected morphological parameters. At steps 406-408, the pacer/ICD detects new values of the selected morphological parameters, measures their deviations from the baseline, and compares those deviations to the current condition-specific detection thresholds to detect the abnormal condition. Additionally, the device collects data within a multidimensional histogram so as to permit the thresholds to be further adjusted, if needed.

FIG. 15 illustrates the multidimensional histogram, 409, particularly illustrating the use of different conditions: heart rate, activity level, posture, time of day. It should be understood that different cells are defined for each combination of different conditions, as well as for various ranges of the morphological parameters. For example, for the range of ST segment deviation from 0% to 1% from baseline for use in detecting cardiac ischemia, there is one histogram cell corresponding to the combination of heart rate:high, activity level:high, posture:supine and time of day:morning; another cell for the combination of heart rate:medium, activity level:high, posture:supine and time of day:morning; yet another cell for the combination of heart rate:low, activity level:high, posture:supine and time of day:morning; and so on. Similarly, there are separate cells for each combination of conditions within the range of ST segment deviation from 1% to 2% from baseline, and so on. As can be appreciated, a fairly large number of cells may be required to accommodate all possible combinations of detection conditions and ranges of deviation. For devices with limited memory, a smaller multidimensional histogram may instead be used that tracks only certain selected combination of conditions. That is, unique thresholds may be specified only for certain combinations of conditions that merit such treatment; whereas, for other combinations of detection conditions, the techniques of FIGS. 10-13 are instead used wherein the thresholds do not distinguish among detection conditions.

If the abnormal condition is detected using the condition-specific thresholds, step 410, then, as before, warnings are delivered and appropriate therapies are also initiated, at step 412, depending upon the abnormal conditions detected, the device programming and the capabilities of the device. Also, as before, diagnostics data is recorded for subsequent physician review. Prior to delivering therapy or generating warnings, the pacer/ICD may corroborate the detection of the condition using other detection techniques. If however, the various deviation values remained within their condition-specific thresholds, then step 414 is instead performed where the pacer/ICD determines if an adjustment to the threshold values is warranted. Assuming that an adjustment is warranted, then the pacer/ICD, at step 416, determines new detection thresholds based on the data in the current multidimensional histogram. Percentiles may again be used to identify the appropriate thresholds for use with the particular patient.

Although described primarily with respect to the detection of abnormal medical conditions based on IEGM parameters, the techniques herein can be applied, where appropriate, to the detection of conditions based on parameters derived from other signals such as impedance measurement signals or physiological sensor signals (e.g. cardiac pressure sensor signals). Insofar as impedance is concerned, ischemia typically can be detected based in impedance measurements. In this regard, ischemia may cause myocardial stunning, which affects contractility of the myocardium. Changes in contractility can be detected based in impedance measurements. Hence, ischemia can be detected based on certain changes in impedance, identified, e.g., based on one or more thresholds. The thresholds may be defined and adjusted using the various techniques described herein. Techniques for detecting contractility based on impedance are discussed in, e.g., U.S. Pat. No. 6,788,970 to Park, et al., entitled "System and method for treating vasovagal syncope using cardiac pacing." See, also, U.S. Patent Application 2005/0240233 of Lippert, et al., entitled "Electrotherapy device." Particularly effective "triphasic" impedance pulses for use in detecting impedance are discussed in U.S. patent application Ser. No. 11/558,194, of Panescu et al., filed Nov. 9, 2006, entitled "Closed-Loop Adaptive Adjustment of Pacing Therapy Based on Cardiogenic Impedance Signals Detected by an Implantable Medical Device."

Insofar as physiological sensors are concerned, a wide variety of sensors may be exploited to detect various physiological signals from which abnormal medical conditions can be detected, such as sensors for detecting blood oxygen saturation $SO_2$, left atrial pressure (LAP), heart sounds, arterial blood pressure (BP), stroke volume, and cardiac output (CO). Where appropriate, thresholds defined for use with those signals may be set and adjusted using the techniques described herein. Techniques for detecting blood oxygen saturation using an implantable medical device are described in: U.S. patent application Ser. No. 11/378,604, of Kroll et al., filed Mar. 16, 2006, entitled, "System and Method for Detecting Arterial Blood Pressure based on Aortic Electrical Resistance using an Implantable Medical Device." Techniques for detecting blood pressure are described in: U.S. Pat. No. 5,615,684 to Hagel, et al., entitled "Medical Device for Detecting Hemodynamic Conditions of a Heart" and U.S. Pat. No. 6,575,912 to Turcott, entitled "Assessing Heart Failure Status Using Morphology of a Signal Representative of Arterial Pulse Pressure." Techniques for detecting stroke volume and/or cardiac output are described in U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle." Techniques for detecting $SO_2$ are described in U.S. Pat. No. 5,676,141 to Hollub, entitled "Electronic Processor for Pulse Oximeters." Depending upon the particular application, either arterial $SO_2$ (i.e. $SaO_2$), or venous $SO_2$ (i.e. $SvO_2$), or both, may be detected and exploited. LAP sensors are discussed in U.S. Published Patent Application 2006/0149155 of Hedberg, entitled "Detection of Diastolic Heart Failure." See also, U.S. Published Patent Application 2006/0009810 of Mann et al. entitled "Method for Detecting, Diagnosing, and Treating Cardiovascular Disease," as well as U.S. Published Patent Application 2006/0149331 also to Mann et al., entitled "Method for Digital Cardiac Rhythm Management." Still further techniques are discussed in U.S. application Ser. No. 11/559,235 to Gutfinger et al., entitled "System and Method for Estimating Cardiac Pressure Using Parameters Derived from Impedance Signals Detected by an Implantable Medical Device," filed Nov. 13, 2006.

What have been described are various techniques for setting and adjusting detection thresholds for use in detecting abnormal physiological conditions within a patient. For the sake of completeness, a description of an exemplary pacer/ICD will now be provided. As many patients who suffer from cardiac ischemia and other abnormal physiological conditions are also candidates for pacer/ICDs, it is advantageous to configure a pacer/ICD to serve as the controller of the abnormal physiological detection system. The techniques of the invention, however, may be performed using any suitable implantable components.

Exemplary Pacer/ICD

FIG. 16 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of detecting cardiac ischemia and/or other abnormal physiological conditions and for controlling the delivery of therapy and warnings in response thereto. To provide atrial chamber pacing stimulation and sensing, pacer/ICD 10 is shown in electrical communication with a heart 512 by way of a left atrial lead 520 having an atrial tip electrode 522 and an atrial ring electrode 523 implanted in the atrial appendage. Pacer/ICD 10 is also in electrical communication with the heart by way of a right ventricular lead 530 having, in this embodiment, a ventricular tip electrode 532, a right ventricular ring electrode 534, a right ventricular (RV) coil electrode 536, and a superior vena cava (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 524 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 524 is designed to receive atrial and ventricular cardiac signals and to deliver left ventricular pacing therapy using at least a left ventricular tip electrode 526, left atrial pacing therapy using at least a left atrial ring electrode 527, and shocking therapy using at least a left atrial coil electrode 528. With this configuration, biventricular pacing can be performed. Although only three leads are shown in FIG. 16, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 17:
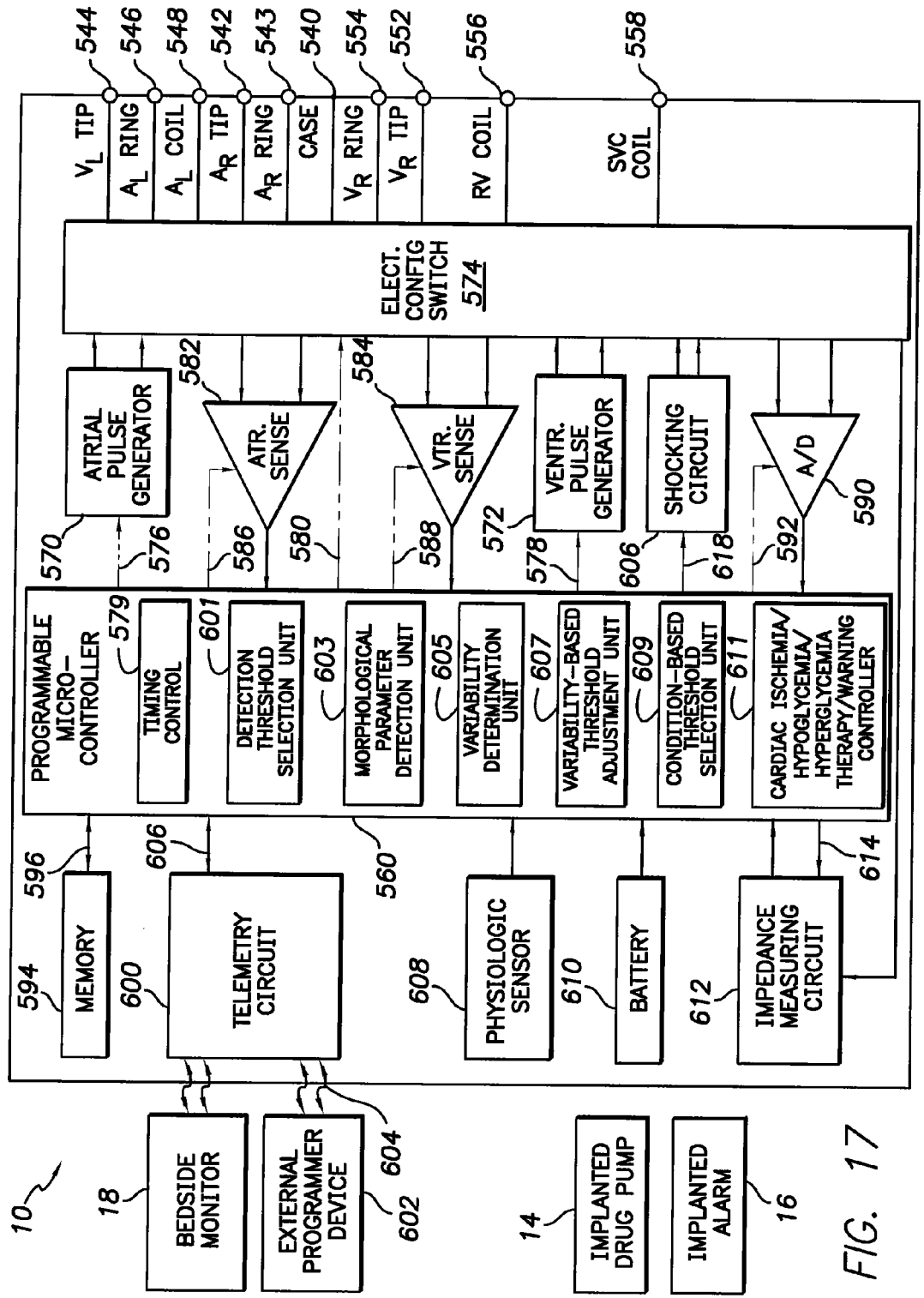
FIG. 17 is a functional block diagram of the pacer/ICD of FIG. 16, illustrating basic circuit elements that provide cardioversion, defibrillation and/or pacing stimulation in the heart and particularly illustrating components for adaptively adjusting detection thresholds.

A simplified block diagram of internal components of pacer/ICD 10 is shown in FIG. 17. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 540 for pacer/ICD 10, shown schematically in FIG. 17, is often referred to as the "can", "case" or "case electrode" and may be programmably selected to act as the return electrode for all "unipolar" modes. The housing 540 may further be used as a return electrode alone or in combination with one or more of the coil electrodes, 528, 536 and 538, for shocking purposes. The housing 540 further includes a connector (not shown) having a plurality of terminals, 542, 543, 544, 546, 548, 552, 554, 556 and 558 (shown schematically and, for convenience, the names of the electrodes to which they are connected are shown next to the terminals). As such, to achieve right atrial sensing and pacing, the connector includes at least a right atrial tip terminal ($A_R$ TIP) 542 adapted for connection to the atrial tip electrode 522 and a right atrial ring ($A_R$ RING) electrode 543 adapted for connection to right atrial ring electrode 523. To achieve left chamber sensing, pacing and shocking, the connector includes at least a left ventricular tip terminal ($V_L$ TIP) 544, a left atrial ring terminal ($A_L$ RING) 546, and a left atrial shocking terminal ($A_L$ COIL) 548, which are adapted for connection to the left ventricular ring electrode 526, the left atrial tip electrode 527, and the left atrial coil electrode 528, respectively. To support right chamber sensing, pacing and shocking, the connector further includes a right ventricular tip terminal ($V_R$ TIP) 552, a right ventricular ring terminal ($V_R$ RING) 554, a right ventricular shocking terminal ($R_V$ COIL) 556, and an SVC shocking terminal (SVC COIL) 558, which are adapted for connection to the right ventricular tip electrode 532, right ventricular ring electrode 534, the RV coil electrode 536, and the SVC coil electrode 538, respectively.

At the core of pacer/ICD 10 is a programmable microcontroller 560, which controls the various modes of stimulation therapy. As is well known in the art, the microcontroller 560 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 560 includes the ability to process or monitor input signals (data) as controlled by a program code stored in a designated block of memory. The details of the design and operation of the microcontroller 560 itself are not critical to the invention. Rather, any suitable microcontroller 560 may be used that carries out the functions described herein. The use of microprocessor-based control circuits for performing timing and data analysis functions are well known in the art.

As shown in FIG. 17, an atrial pulse generator 570 and a ventricular/impedance pulse generator 572 generate pacing stimulation pulses for delivery by the right atrial lead 520, the right ventricular lead 530, and/or the coronary sinus lead 524 via an electrode configuration switch 574. It is understood that in order to provide stimulation therapy in each of the four chambers of the heart, the atrial and ventricular pulse generators, 570 and 572, may include dedicated, independent pulse generators, multiplexed pulse generators or shared pulse generators. The pulse generators, 570 and 572, are controlled by the microcontroller 560 via appropriate control signals, 576 and 578, respectively, to trigger or inhibit the stimulation pulses.

The microcontroller 560 further includes timing control circuitry 579 used to control the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 574 includes a plurality of switches for connecting the desired electrodes to the appropriate I/O circuits, thereby providing complete electrode programmability. Accordingly, the switch 574, in response to a control signal 580 from the microcontroller 560, determines the polarity of the stimulation pulses (e.g., unipolar, bipolar, combipolar, etc.) by selectively closing the appropriate combination of switches (not shown) as is known in the art.

Atrial sensing circuits 582 and ventricular sensing circuits 584 may also be selectively coupled to the right atrial lead 520, coronary sinus lead 524, and the right ventricular lead 530, through the switch 574 for detecting the presence of cardiac activity in each of the four chambers of the heart. Accordingly, the atrial (ATR. SENSE) and ventricular (VTR. SENSE) sensing circuits, 582 and 584, may include dedicated sense amplifiers, multiplexed amplifiers or shared amplifiers. The switch 574 determines the "sensing polarity" of the cardiac signal by selectively closing the appropriate switches, as is also known in the art. In this way, the clinician may program the sensing polarity independent of the stimulation polarity. Each sensing circuit, 582 and 584, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 582 and 584, are connected to the microcontroller 560 which, in turn, are able to trigger or inhibit the atrial and ventricular pulse generators, 570 and 572, respectively, in a demand fashion in response to the absence or presence of cardiac activity in the appropriate chambers of the heart.

For arrhythmia detection, pacer/ICD 10 utilizes the atrial and ventricular sensing circuits, 582 and 584, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 560 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 590. The data acquisition system 590 is configured to acquire intracardiac electrogram signals, convert the raw analog data into a digital signal, and store the digital signals for later processing and/or telemetric transmission to an external device 602. The data acquisition system 590 is coupled to the right atrial lead 520, the coronary sinus lead 524, and the right ventricular lead 530 through the switch 574 to sample cardiac signals across any pair of desired electrodes. The microcontroller 560 is further coupled to a memory 594 by a suitable data/address bus 596, wherein the programmable operating parameters used by the microcontroller 560 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 594 through a telemetry circuit 600 in telemetric communication with the external device 602, such as a programmer, transtelephonic transceiver or a diagnostic system analyzer. The telemetry circuit 600 is activated by the microcontroller by a control signal 606. The telemetry circuit 600 advantageously allows intracardiac electrograms and status information relating to the operation of pacer/ICD 10 (as contained in the microcontroller 560 or memory 594) to be sent to the external device 602 through an established communication link 604. Pacer/ICD 10 further includes an accelerometer or other physiologic sensor 608, commonly referred to as a "rate-responsive" sensor because it is typically used to adjust pacing stimulation rate according to the exercise state of the patient. However, the physiological sensor 608 may further be used to detect changes in cardiac output, changes in the physiological condition of the heart, or diurnal changes in activity (e.g., detecting sleep and wake states) and to detect arousal from sleep. Accordingly, the microcontroller 560 responds by adjusting the various pacing parameters (such as rate, AV Delay, V-V Delay, etc.) at which the atrial and ventricular pulse generators, 570 and 572, generate stimulation pulses. While shown as being included within pacer/ICD 10, it is to be understood that the physiologic sensor 608 may also be external to pacer/ICD 10, yet still be implanted within or carried by the patient. A common type of rate responsive sensor is an activity sensor incorporating an accelerometer or a piezoelectric crystal, which is mounted within the housing 540 of pacer/ICD 10. Other types of physiologic sensors are also known, for example, sensors that sense the oxygen content of blood, respiration rate and/or minute ventilation, pH of blood, ventricular gradient, patient posture, LAP, arterial BP, stroke volume, cardiac output, etc.

The pacer/ICD additionally includes at least one battery 610 of other power source, which provides operating power to all of the circuits shown in FIG. 17. The battery 610 may vary depending on the capabilities of pacer/ICD 10. If the system only provides low voltage therapy, a lithium iodine or lithium copper fluoride cell may be utilized. For pacer/ICD 10, which employs shocking therapy, the battery 610 must be capable of operating at low current drains for long periods, and then be capable of providing high-current pulses (for capacitor charging) when the patient requires a shock pulse. The battery 610 must also have a predictable discharge characteristic so that elective replacement time can be detected. Accordingly, pacer/ICD 10 is preferably capable of high voltage therapy and appropriate batteries.

As further shown in FIG. 17, pacer/ICD 10 includes an impedance measuring circuit 612 that is enabled by the microcontroller 560 via a control signal 614. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 612 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 560 further controls a shocking circuit 616 by way of a control signal 618. The shocking circuit 616 generates shocking pulses of low (up to 0.5 joules), moderate (0.5-10 joules) or high energy (11 to 40 joules), as controlled by the microcontroller 560. Such shocking pulses are applied to the heart of the patient through at least two shocking electrodes, and as shown in this embodiment, selected from the left atrial coil electrode 528, the RV coil electrode 536, and/or the SVC coil electrode 538. The housing 540 may act as an active electrode in combination with the RV electrode 536, or as part of a split electrical vector using the SVC coil electrode 538 or the left atrial coil electrode 528 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 560 is capable of controlling the synchronous or asynchronous delivery of the shocking pulses.

Microcontroller 560 also includes various components directed to the detecting cardiac ischemia via pattern recognition and for controlling delivery of therapy and warnings in response thereto. In particular, the pacer/ICD includes a detection threshold selection unit 601 operative to set detection thresholds to default values determined, e.g., using the techniques of FIG. 5. Electrical cardiac signals are sensed within the patient using the atrial and ventricular sense amps, 582, 594, respectively. Impedance signals may be sensed, where appropriate, using impedance circuit 612. One or more physiological signals may be sensed, where appropriate, using sensor 608, which, as already noted, need not be installed inside the housing of the pacer/ICD, but may be implanted elsewhere in the patient. A morphological parameter detection unit 603 is operative to derive values of morphological parameters (such as those parameters illustrated in FIG. 3) from the sensed signals for use in applying to the thresholds to detect abnormal physiological conditions. A variability determination unit 605 is operative to determine an amount of variation in the morphological parameters within the patient, and a variability-based threshold adjustment unit 607 is operative to adjust the detection thresholds based, in part, on the amount of variation in the morphological parameters within the patient, in accordance with the techniques of, e.g., FIGS. 8 and 10. A condition-based threshold selection unit 609 may additionally be employed that is operative to select and adjust particular detection thresholds based on current patient conditions such as heart rate, activity level, posture, etc., in accordance with the techniques of FIG. 13. Histograms used by these various components may be stored within memory 594. A cardiac ischemia/hypoglycemia/hyperglycemia therapy/warning controller 611 controls delivery of therapy and/or warning signals in response to the detection of ischemia, hypoglycemia, and/or hyperglycemia or other abnormal medical conditions, again in accordance with techniques already described. Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, as hardware devices.

In general, a wide variety of techniques can be implemented consistent with the principles the invention and no attempt is made herein to describe all possible techniques. Although described primarily with reference to an example wherein the implanted device is a pacer/ICD, principles of the invention are applicable to other implantable medical devices as well. In addition, whereas many of the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia or other conditions within any of those patients. In such an implementation, the central processing device then transmits appropriate warning signals to the bedside monitor of the patient for warning the patient and additionally transmits appropriate warning signals to the physician associated with the patient or a third party such as emergency medical service (EMS) personnel.

The various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to."

What is claimed is:

1. A method for use with an implantable medical device having a detection system that detects an abnormal physiological condition within a patient in which the device is implanted by comparing at least one morphological parameter against a detection threshold, wherein the morphological parameter is derived from signals sensed within the patient, the method comprising:

sensing signals within the patient and deriving values of the morphological parameter from the signals;

monitoring the values of the morphological parameter to detect a possible occurrence of the abnormal physiological condition;

collecting information representative of a range of variation in the morphological parameter within the patient;

adjusting the detection threshold based on the information representative of the range of variation in the morphological parameter collected within the patient to improve detection accuracy; and wherein collecting information representative of a range of variation in the morphological parameter within the patient includes:

selectively incrementing a plurality of counters based on the plurality of measurements, wherein the counters are representative of different ranges of measurements.

2. The method of claim 1 further including the initial step of setting the detection threshold to a default value and wherein the step of monitoring the values of the morphological parameter to detect a possible occurrence of the abnormal physiological condition includes comparing the values to the default detection threshold.

3. The method of claim 1 wherein the morphological parameter derived from the signals includes values derived from electrical cardiac signals including one or more of: atrial depolarization events (P-waves), ventricular depolarization events (QRS-complexes), and ventricular repolarization events (T-waves).

4. The method of claim 1 wherein the steps of monitoring the values of the morphological parameter to detect a possible occurrence of the abnormal physiological condition and collecting information representative of the range of variation in the morphological parameter within the patient are performed during an initial learning period following device implant.

5. The method of claim 1 wherein information is separately collected for each of a plurality of different morphological parameters.

6. The method of claim 1 wherein the threshold is adjusted periodically based on newly detected variations in the morphological parameter within the patient.

7. The method of claim 1 wherein the abnormal physiological condition to be detected includes one or more of: cardiac ischemia, hypoglycemia and hyperglycemia.

8. The method of claim 1 further including a reinitialization procedure including the steps of resetting the thresholds and repeating one or more of the steps of: sensing signals within the patient and deriving values of the morphological parameter from the signals; monitoring the values of the morphological parameter to detect a possible occurrence of the abnormal physiological condition; collecting information representative of a range of variation in the morphological parameter within the patient; and adjusting the detection threshold based on the information representative of the range of variation in the morphological parameter collected within the patient to improve detection accuracy.

9. A method for use with an implantable medical device having a detection system that detects an abnormal physiological condition within a patient in which the device is implanted by comparing at least one morphological parameter against a detection threshold, wherein the morphological parameter is derived from signals sensed within the patient, the method comprising:

sensing signals within the patient and deriving values of the morphological parameter from the signals;

monitoring the values of the morphological parameter to detect a possible occurrence of the abnormal physiological condition;

collecting information representative of a range of variation in the morphological parameter within the patient;

adjusting the detection threshold based on the information representative of the range of variation in the morphological parameter collected within the patient to improve detection accuracy; and wherein adjusting the threshold based on the information collected within the patient is performed to achieve a target percentile value within a range of variation in the morphological parameter observed within the patient.

10. A method for use with an implantable medical device having a detection system that detects an abnormal physiological condition within a patient in which the device is implanted by comparing at least one morphological parameter against a detection threshold, wherein the morphological parameter is derived from signals sensed within the patient, the method comprising:

sensing signals within the patient and deriving values of the morphological parameter from the signals;

monitoring the values of the morphological parameter to detect a possible occurrence of the abnormal physiological condition;

collecting information representative of a range of variation in the morphological parameter within the patient;

adjusting the detection threshold based on the information representative of the range of variation in the morphological parameter collected within the patient to improve detection accuracy;

wherein a plurality of detection thresholds are specified for use under different conditions, and wherein the plurality of detection thresholds are independently set and adjusted based on the range of variation of the morphological parameter during the different conditions.

11. A method for use with an implantable medical device having a detection system that detects an abnormal physiological condition within a patient in which the device is implanted by comparing at least one morphological parameter against a detection threshold, wherein the morphological parameter is derived from signals sensed within the patient, the method comprising:

sensing signals within the patient and deriving values of the morphological parameter from the signals;

monitoring the values of the morphological parameter to detect a possible occurrence of the abnormal physiological condition;

collecting information representative of a range of variation in the morphological parameter within the patient;

adjusting the detection threshold based on the information representative of the range of variation in the morphological parameter collected within the patient to improve detection accuracy; and wherein the detection thresholds include persistence-based thresholds.

* * * * *